United States Patent
Morton et al.

(10) Patent No.: US 9,161,823 B2
(45) Date of Patent: Oct. 20, 2015

(54) ORTHODONTIC SYSTEMS AND METHODS INCLUDING PARAMETRIC ATTACHMENTS

(75) Inventors: John Morton, San Jose, CA (US); Vadim Matov, San Jose, CA (US); Heng Cao, San Jose, CA (US); Ryan Kimura, San Jose, CA (US); Jihua Cheng, Cupertino, CA (US); Bastien Pesenti, Santa Clara, CA (US)

(73) Assignee: Align Technology, Inc., San Jose, CA (US)

( * ) Notice: Subject to any disclaimer, the term of this patent is extended or adjusted under 35 U.S.C. 154(b) by 1019 days.

(21) Appl. No.: 12/623,340

(22) Filed: Nov. 20, 2009

(65) Prior Publication Data

US 2010/0138025 A1    Jun. 3, 2010

Related U.S. Application Data

(60) Provisional application No. 61/242,379, filed on Sep. 14, 2009, provisional application No. 61/116,448, filed on Nov. 20, 2008.

(51) Int. Cl.
*A61C 3/00* (2006.01)
*A61C 7/00* (2006.01)
(Continued)

(52) U.S. Cl.
CPC ... *A61C 7/00* (2013.01); *A61C 7/08* (2013.01); *A61C 7/14* (2013.01); *A61C 7/002* (2013.01)

(58) Field of Classification Search
CPC .......... A61C 7/00; A61C 7/002; A61C 7/146; A61C 9/004; A61C 13/0004
USPC ....................................... 433/2–24
See application file for complete search history.

(56) References Cited

U.S. PATENT DOCUMENTS

| | | | |
|---|---|---|---|
| 2,467,432 A | 4/1949 | Kesling | |
| 3,407,500 A * | 10/1968 | Kesling | ............................. 433/6 |

(Continued)

FOREIGN PATENT DOCUMENTS

| | | |
|---|---|---|
| AU | 3031677 | 5/1979 |
| AU | 517102 | 7/1981 |

(Continued)

OTHER PUBLICATIONS

Andrews, The Six Keys to Optimal Occlusion Straight Wire, Chapter 3, pp. 13-24 (1989).

(Continued)

*Primary Examiner* — Cris L Rodriguez
*Assistant Examiner* — Matthew Saunders
(74) *Attorney, Agent, or Firm* — Wilson Sonsini Goodrich & Rosati

(57) ABSTRACT

Orthodontic systems and related methods are disclosed for designing and providing improved or more effective tooth moving systems for eliciting a desired tooth movement and/or repositioning teeth into a desired arrangement. Methods and orthodontic systems of the invention include tooth attachments having improved or optimized parameters selected or modified for more optimal and/or effective application of forces for a desired/selected orthodontic movement. Attachments of the present invention can be customized to a particular patient (e.g., patient-customized), a particular movement, and/or a sub-group or sub-set of patients, and configured to engage an orthodontic tooth positioning appliance worn by a patient, where engagement between the attachment and orthodontic appliance results in application of a repositioning force or series/system of forces to the tooth having the attachment and will generally elicit a tooth movement.

25 Claims, 33 Drawing Sheets

(51) Int. Cl.
  *A61C 7/08* (2006.01)
  *A61C 7/14* (2006.01)

(56) References Cited

U.S. PATENT DOCUMENTS

| | | | |
|---|---|---|---|
| 3,600,808 A | 8/1971 | Reeve | |
| 3,660,900 A | 5/1972 | Andrews | |
| 3,683,502 A | 8/1972 | Wallshein | |
| 3,738,005 A | 6/1973 | Cohen | |
| 3,803,715 A * | 4/1974 | Wallshein | 433/18 |
| 3,860,803 A | 1/1975 | Levine | |
| 3,916,526 A | 11/1975 | Schudy | |
| 3,922,786 A | 12/1975 | Lavin | |
| 3,950,851 A | 4/1976 | Bergersen | |
| 3,983,628 A | 10/1976 | Acevedo | |
| 4,014,096 A | 3/1977 | Dellinger | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |
| 4,575,330 A | 3/1986 | Hull | |
| 4,575,805 A | 3/1986 | Moermann et al. | |
| 4,591,341 A * | 5/1986 | Andrews | 433/6 |
| 4,609,349 A | 9/1986 | Cain | |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,836,778 A | 6/1989 | Baumrind et al. | |
| 4,837,732 A | 6/1989 | Brandestini et al. | |
| 4,850,864 A | 7/1989 | Diamond | |
| 4,850,865 A | 7/1989 | Napolitano | |
| 4,856,991 A * | 8/1989 | Breads et al. | 433/6 |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,935,635 A | 6/1990 | O'Harra | |
| 4,936,862 A | 6/1990 | Walker et al. | |
| 4,937,928 A | 7/1990 | van der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A | 4/1991 | Lemchen | |
| 5,017,133 A | 5/1991 | Miura | |
| 5,027,281 A | 6/1991 | Rekow et al. | |
| 5,035,613 A * | 7/1991 | Breads et al. | 433/6 |
| 5,055,039 A * | 10/1991 | Abbatte et al. | 433/24 |
| 5,059,118 A * | 10/1991 | Breads et al. | 433/6 |
| 5,100,316 A | 3/1992 | Wildman | |
| 5,121,333 A | 6/1992 | Riley et al. | |
| 5,125,832 A | 6/1992 | Kesling | |
| 5,128,870 A | 7/1992 | Erdman et al. | |
| 5,130,064 A | 7/1992 | Smalley | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A | 9/1992 | Martz et al. | |
| 5,176,517 A | 1/1993 | Truax | |
| 5,184,306 A | 2/1993 | Erdman et al. | |
| 5,186,623 A * | 2/1993 | Breads et al. | 433/6 |
| 5,203,700 A * | 4/1993 | Chmel | 433/169 |
| 5,257,203 A | 10/1993 | Riley et al. | |
| 5,273,429 A | 12/1993 | Rekow et al. | |
| 5,278,756 A | 1/1994 | Lemchen et al. | |
| 5,328,362 A | 7/1994 | Watson et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| RE35,169 E | 3/1996 | Lemchen et al. | |
| 5,518,397 A | 5/1996 | Andreiko et al. | |
| 5,528,735 A | 6/1996 | Strasnick et al. | |
| 5,533,895 A * | 7/1996 | Andreiko et al. | 433/24 |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Andersson et al. | |
| 5,605,459 A | 2/1997 | Kuroda et al. | |
| 5,607,305 A | 3/1997 | Andersson et al. | |
| 5,614,075 A | 3/1997 | Andre | |
| 5,621,648 A | 4/1997 | Crump | |
| 5,645,420 A | 7/1997 | Bergersen | |
| 5,645,421 A | 7/1997 | Slootsky | |
| 5,655,653 A | 8/1997 | Chester | |
| 5,683,243 A | 11/1997 | Andreiko et al. | |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A | 1/1999 | van Nifterick et al. | |
| 5,866,058 A | 2/1999 | Batchelder et al. | |
| 5,879,158 A * | 3/1999 | Doyle et al. | 433/24 |
| 5,880,961 A | 3/1999 | Crump | |
| 5,880,962 A | 3/1999 | Andersson et al. | |
| 5,934,288 A | 8/1999 | Avila et al. | |
| 5,957,686 A | 9/1999 | Anthony | |
| 5,964,587 A * | 10/1999 | Sato | 433/6 |
| 5,971,754 A | 10/1999 | Sondhi et al. | |
| 5,975,893 A * | 11/1999 | Chishti et al. | 433/6 |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 * | 6/2002 | Ernst | 600/590 |
| 6,482,298 B1 | 11/2002 | Bhatnagar | |
| 6,524,101 B1 | 2/2003 | Phan et al. | |
| 6,554,611 B2 | 4/2003 | Chishti et al. | |
| 6,554,613 B1 * | 4/2003 | Sachdeva et al. | 433/24 |
| 6,572,372 B1 | 6/2003 | Phan et al. | |

(56) References Cited

U.S. PATENT DOCUMENTS

| | | | |
|---|---|---|---|
| 6,629,840 | B2 | 10/2003 | Chishti et al. |
| 6,705,863 | B2* | 3/2004 | Phan et al. ............... 433/24 |
| 6,722,880 | B2 | 4/2004 | Chishti et al. |
| 6,918,761 | B2* | 7/2005 | Sachdeva et al. .......... 433/24 |
| 7,063,533 | B2* | 6/2006 | Phan et al. ................ 433/24 |
| 7,125,248 | B2* | 10/2006 | Phan et al. ................. 433/6 |
| 7,234,934 | B2* | 6/2007 | Rosenberg ................. 433/6 |
| 7,374,421 | B2* | 5/2008 | Solomon .................. 433/18 |
| 2001/0002310 | A1* | 5/2001 | Chishti et al. ............ 433/24 |
| 2002/0006597 | A1 | 1/2002 | Andreiko et al. |
| 2003/0009252 | A1 | 1/2003 | Pavlovskaia et al. |
| 2003/0139834 | A1 | 7/2003 | Nikolskiy et al. |
| 2003/0198911 | A1* | 10/2003 | Knopp et al. ............... 433/6 |
| 2003/0224311 | A1 | 12/2003 | Cronauer |
| 2004/0128010 | A1 | 7/2004 | Pavlovskaia et al. |
| 2005/0055118 | A1 | 3/2005 | Nikolskiy et al. |
| 2005/0106525 | A1* | 5/2005 | Knopp et al. ............... 433/6 |
| 2005/0277084 | A1* | 12/2005 | Cinader et al. .............. 433/20 |
| 2006/0177789 | A1* | 8/2006 | O'Bryan ..................... 433/6 |
| 2006/0223022 | A1* | 10/2006 | Solomon .................... 433/6 |
| 2006/0223023 | A1* | 10/2006 | Lai et al. ................... 433/24 |
| 2008/0109198 | A1* | 5/2008 | Knopp et al. ............. 703/11 |
| 2008/0227050 | A1* | 9/2008 | Marshall .................. 433/24 |
| 2009/0191503 | A1* | 7/2009 | Matov et al. .............. 433/24 |

FOREIGN PATENT DOCUMENTS

| | | |
|---|---|---|
| AU | 5598894 | 6/1994 |
| CA | 1121955 | 4/1982 |
| DE | 2749802 | 5/1978 |
| DE | 69327661 | 7/2000 |
| EP | 0091876 | 10/1983 |
| EP | 0299490 | 1/1989 |
| EP | 0376873 | 7/1990 |
| EP | 0490848 | 6/1992 |
| EP | 0541500 | 5/1993 |
| EP | 0667753 | 8/1995 |
| EP | 0731673 | 9/1996 |
| EP | 0774933 | 5/1997 |
| ES | 463897 | 1/1980 |
| FR | 2369828 | 6/1978 |
| FR | 2652256 | 3/1991 |
| GB | 1550777 | 8/1979 |
| JP | 53-058191 | 5/1978 |
| JP | 04-028359 | 1/1992 |
| JP | 08-508174 | 9/1996 |
| WO | WO 90/08512 | 8/1990 |
| WO | WO 91/04713 | 4/1991 |
| WO | WO 94/10935 | 5/1994 |
| WO | WO 98/32394 | 7/1998 |
| WO | WO 98/44865 | 10/1998 |
| WO | WO 98/58596 | 12/1998 |

OTHER PUBLICATIONS

Biostar Operation & Training Manual. Great Lakes Orthodontics, Ltd. 199 Fire Tower Drive, Tonawanda, New York. 14150-5890, 20 pages total (1990).
Dentrac Corporation, Dentrac document, pp. 4-13 (1992).
DuraClearTM product information, Allesee Orthodontic Appliances-Pro Lab, 1 page (1997).
Gim-Alldent Deutschland, "Das DUX System: Die Technik," 2 pages total (2002).
Important Tip About Wearing the Red White & Blue Active Clear Retainer System, Allesee Orthodontic Appliances-Pro Lab, 1 page; 1998.
Siemens, "CEREC—Computer-Reconstruction," High Tech in der Zahnmedizin, 14 pages total (2004).
The Red, White & Blue Way to Improve Your Smile!Allesee Orthodontic Appliances-Pro Lab product information for patients, 2 pages; 1992.
Tru-Tain Orthodontic & Dental Supplies, Product Brochure, Rochester, Minnesota 55902, 16 pages total (1996).
Warunek et.al., Clinical Use of Silicone Elastomer Applicances, JCO (1989) XXIII(10):694-700.
You May Be a Candidate for This Invisible No-Braces Treatment, Allesee Orthodontic Appliances-Pro Lab product information for patients, 2 pages (2002).
Alcaniz, et al., "An Advanced System for the Simulation and Planning of Orthodontic Treatments," Karl Heinz Hohne and Ron Kikinis (eds.), *Visualization in Biomedical Computing, 4th Int'l. Conf., VBC '96, Hamburg, Germany*, Sep. 22-25, 1996, Springer-Verlag, pp. 511-520.
"Important Tip About Wearing the Red White & Blue Active Clear Retainer System," Allesee Orthodontic Appliances-Pro Lab, 1 page.
"Inside the ADA," *JADA*, 118:286-294 (Mar. 1989).
"The Choice Is Clear: Red, White & Blue . . . The Simple, Affordable, No-Braces Treatment," Allesee Orthodontic Appliances-Pro Lab product information for doctors, <http://ormco.com/aoa/appliancesservices/RWB/doctor.html>, 5 pages (May 19, 2003).
"The Choice is Clear: Red, White & Blue . . . The Simple, Affordable, No-Braces Treatment," Allesee Orthodontic Appliances-Pro Lab product information for patients, <http://ormco.com/aoa/appliancesservices/RWB/patients.html>, 2 pages (May 19, 2003).
"The Choice Is Clear: Red, White & Blue . . . The Simple, Affordable, No-Braces Treatment," Allesee Orthodontic Appliances-Pro Lab product information, 6 pages (2003).
"The Red, White & Blue Way to Improve Your Smile!" Allesee Orthodontic Appliances-Pro Lab product information for patients, 2 pages.
"You May Be a Candidate for This Invisible No-Braces Treatment," Allesee Orthodontic Appliances-Pro Lab product information for patients, 2 pages.
Alexander et al., "The DigiGraph Work Station Part 2 Clinical Management," *JCO*, pp. 402-407 (Jul. 1990).
Altschuler et al., "Measuring Surfaces Space-Coded by a Laser-Projected Dot Matrix," *SPIE Imaging Applications for Automated Industrial Inspection and Assembly*, vol. 182, p. 187-191 (1979).
Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.
Altschuler et al., "Laser Electro-Optic System for Rapid Three-Dimensional (3D) Topographic Mapping of Surfaces," *Optical Engineering*, 20(6):953-961 (1981).
Altschuler, "3D Mapping of Maxillo-Facial Prosthesis," AADR Abstract #607, 2 pages total, (1980).
American Association for Dental Research, Summary of Activities, Mar. 20-23,1980, Los Angeles, CA, p. 195.
Andersson et al., "Clinical Results with Titanium Crowns Fabricated with Machine Duplication and Spark Erosion," *Acta. Odontol. Scand.*, 47:279-286 (1989).
Andrews, *The Six Keys to Optimal Occlusion Straight Wire*, Chapter 3, pp. 13-24.
Bartels, et al., *An Introduction to Splines for Use in Computer Graphics and Geometric Modeling*, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, *SPIE*, vol. 166, pp. 112-123.
Baumrind et al., "Mapping the Skull in 3-D," reprinted from *J. Calif. Dent. Assoc.*, 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," *Semin. in Orthod.*, 7(4):223-232 (Dec. 2001).
Begole et al., "A Computer System for the Analysis of Dental Casts," *The Angle Orthod.*, 51(3):253-259 (Jul. 1981).

(56) References Cited

OTHER PUBLICATIONS

Bernard et al., "Computerized Diagnosis in Orthodontics for Epidemiological Studies: A Progress Report," Abstract, *J. Dental Res. Special Issue*, vol. 67, p. 169, paper presented at International Association for Dental Research 66th General Session, Mar. 9-13, 1988, Montreal, Canada.
Bhatia et al., "A Computer-Aided Design for Orthognathic Surgery," *Br. J. Oral Maxillofac. Surg.*, 22:237-253 (1984).
Biggerstaff et al., "Computerized Analysis of Occlusion in the Postcanine Dentition," *Am. J. Orthod.*, 61(3): 245-254 (Mar. 1972).
Biggerstaff, "Computerized Diagnostic Setups and Simulations," *Angle Orthod.*, 40(1):28-36 (Jan. 1970).
Biostar Opeation & Training Manual. Great Lakes Orthodontics, Ltd. 199 Fire Tower Drive, Tonawanda, New York. 14150-5890. 20 pages total.
Blu, et al., "Linear interpolation revitalized", *IEEE Trans. Image Proc.*, 13(5):710-719 (May 2004).
Bourke, "Coordinate System Transformation," (Jun. 1996), p. 1, retrieved from the Internet Nov. 5, 2004, URL <http://astronomy.swin.edu.au/~pbourke/projection/coords>.
Boyd et al., "Three Dimensional Diagnosis and Orthodontic Treatment of Complex Malocclusions With the Invisalign Appliance," *Semin. Orthod.*, 7(4):274-293 (Dec. 2001).
Brandestini et al., "Computer Machined Ceramic Inlays: In Vitro Marginal Adaptation," *J. Dent. Res. Special Issue*, Abstracts, vol. 64, p. 208 (1985).
Brook et al., "An Image Analysis System for the Determination of Tooth Dimensions from Study Casts: Comparison with Manual Measurements of Mesio-distal Diameter," *J. Dent. Res.*, 65(3):428-431 (Mar. 1986).
Burstone (interview), "Dr. Charles J. Burstone on The Uses of the Computer in Orthodontic Practice (Part 1)," *J. Clin. Orthod.*, 13(7):442-453 (Jul. 1979).
Burstone (interview), "Dr. Charles J. Burstone on The Uses of the Computer in Orthodontic Practice (Part 2)," *J. Clin. Orthod.*, 13(8):539-551 (Aug. 1979).
Burstone et al., Precision Adjustment of the Transpalatal Lingual Arch: Computer Arch Form Predetermination, *Am, Journal of Orthodontics*, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," *JCO*, pp. 360-367 (Jun. 1990).
Chafetz et al., "Subsidence of the Femoral Prosthesis, A Stereophotogrammetric Evaluation," *Clin. Orthop. Relat. Res.*, No. 201, pp. 60-67 (Dec. 1985).
Chiappone, (1980). Constructing the Gnathologic Setup and Positioner, *J. Clin. Orthod*, vol. 14, pp. 121-133.
Cottingham, (1969). Gnathologic Clear Plastic Positioner, *Am. J. Orthod*, vol. 55, pp. 23-31.
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, *Canadian Dental Journal*, vol. 54(9), pp. 661-666 (1988).
Crawford, "CAD/CAM in the Dental Office: Does It Work?", *Canadian Dental Journal*, vol. 57, No. 2, pp. 121-123 (Feb. 1991).
Crooks, "CAD/CAM Comes to USC," *USC Dentistry*, pp. 14-17 (Spring 1990).
Cureton, Correcting Malaligned Mandibular Incisors with Removable Retainers, *J. Clin. Orthod*, vol. 30, No. 7 (1996) pp. 390-395.
Curry et al., "Integrated Three-Dimensional Craniofacial Mapping at the Craniofacial Research Instrumentation Laboratory/University of the Pacific," *Semin. Orthod.*, 7(4):258-265 (Dec. 2001).
Cutting et al., "Three-Dimensional Computer-Assisted Design of Craniofacial Surgical Procedures: Optimization and Interaction with Cephalometric and CT-Based Models," *Plast. Reconstr. Surg.*, 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for "Gingiva," Dictionary.com, pp. 1-3, retrieved from the Internet on Nov. 5, 2004, URL <http://reference.com/search/search?q=gingiva>.
Defranco et al., "Three-Dimensional Large Displacement Analysis of Orthodontic Appliances," *J. Biomechanics*, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13.
Dent-X posted on Sep. 24, 1998 at <http://www.dent-x.com/DentSim.htm>, 6 pages.
Doyle, "Digital Dentistry," *Computer Graphics World*, pp. 50-52, 54 (Oct. 2000).
DuraClear™ product information, Allesee Orthodontic Appliances-Pro Lab, 1 page.
Duret et al, "CAD-CAM in Dentistry," *J. Am. Dent. Assoc.*, 117:715-720 (Nov. 1988).
Duret et al, "CAD/CAM Imaging in Dentistry," *Curr. Opin. Dent.*, 1:150-154 (1991).
Duret, "The Dental CAD/CAM, General Description of the Project," *Hennson International Product Brochure*, 18 pages total, Jan. 1986.
Duret,"Vers Une Prosthese Informatisee," (English translation attached), *Tonus*, vol. 75, pp. 55-57 (Nov. 15, 1985).
Economides, "The Microcomputer in the Orthodontic Office," *JCO*, pp. 767-772 (Nov. 1979).
Elsasser, Some Observations on the History and Uses of the Kesling Positioner, *Am. J. Orthod.* (1950) 36:368-374.
English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," *Am. J. Orthod.*, 73(1):36-46 (Jan. 1978).
Felton et al., "A Computerized Analysis of the Shape and Stability of Mandibular Arch Form," *Am. J. Orthod. Dentofacial Orthop.*, 92(6):478-483 (Dec. 1987).
Friede et al., "Accuracy of Cephalometric Prediction in Orthognathic Surgery," Abstract of Papers, *J. Dent. Res.*, 70:754-760 (1987).
Fütterling et al., "Automated Finite Element Modeling of a Human Mandible with Dental Implants," WSCG '98—Conference Program, retrieved from the Internet: <http://wscg.zcu.cz/wscg98/papers98/Strasser_98.pdf>, 8 pages.
Gao et al., "3-D element Generation for Multi-Connected Complex Dental and Mandibular Structure," Proc. Int'l Workshop on Medical Imaging and Augmented Reality, pp. 267-271 (Jun. 12, 2001).
Gim-Alldent Deutschland, "Das DUX System: Die Technik," 2 pages total.
Gottleib et al, "JCO Interviews Dr. James A. McNamura, Jr., on the Frankel Appliance: Part 2: Clinical Management, " *J. Clin. Orthod.*, 16(6):390-407 (Jun. 1982).
Grayson, "New Methods for Three Dimensional Analysis of Craniofacial Deformity, Symposium: Computerized Facial Imaging in Oral and Maxiiofacial Surgery," *AAOMS*, 3 pages total, (Sep. 13, 1990).
Guess et al., "Computer Treatment Estimates in Orthodontics and Orthognathic Surgery," *JCO*, pp. 262-282 (Apr. 1989).
Heaven et al., "Computer-Based Image Analysis of Artificial Root Surface Caries," Abstracts of Papers, *J. Dent. Res.*, 70:528 (Apr. 17-21, 1991).
Highbeam Research, "Simulating Stress Put on Jaw," Tooling & Production [online], Nov. 1996, pp. 1-2, retrieved from the Internet on Nov. 5, 2004, URL <http://static.highbeam.com/t/toolingamp-production/november011996/simulatingstressputonja . . . >.
Hikage, "Integrated Orthodontic Management System for Virtual Three-Dimensional Computer Graphic Simulation and Optical Video Image Database for Diagnosis and Treatment Planning", *Journal of Japan Orthodontic Society*, Feb. 1987, English translation, pp. 1-38, Japanese version, 46(2), pp. 248-269 (60 pages total).

(56) References Cited

OTHER PUBLICATIONS

Hoffmann, et al., "Role of Cephalometry for Planning of Jaw Orthopedics and Jaw Surgery Procedures," (Article Summary in English, article in German), *Informatbnen*, pp. 375-396 (Mar. 1991).

Hojjatie et al., "Three-Dimensional Finite Element Analysis of Glass-Ceramic Dental Crowns," *J. Biomech.*, 23(11):1157-1166 (1990).

Huckins, "CAD-CAM Generated Mandibular Model Prototype from MRI Data," *AAOMS*, p. 96 (1999).

"JCO Interviews, Craig Andreiko, DDS, MS on the Elan and Orthos Systems," *JCO*, pp. 459- 468 (Aug. 1994).

"JCO Interviews, Dr. Homer W. Phillips on Computers in Orthodontic Practice, Part 2," *JCO*, pp. 819-831 (Dec. 1983).

Jerrold, "The Problem, Electronic Data Transmission and the Law," *AJO-DO*, pp. 478-479 (Apr. 1988).

Jones et al., "An Assessment of the Fit of a Parabolic Curve to Pre- and Post-Treatment Dental Arches," *Br. J. Orthod.*, 16:85-93 (1989).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case Reports, J. Nihon University School of Dentistry (1982) 24(1):1-27.

Kanazawa et al., "Three-Dimensional Measurements of the Occlusal Surfaces of Upper Molars in a Dutch Population," *J. Dent Res.*, 63(11):1298-1301 (Nov. 1984).

Kochanek, "Interpolating Splines with Local Tension, Continuity and Bias Control," *Computer Graphics*, 18(3):33-41 (Jul. 1984).

Kesling et al., The Philosophy of the Tooth Positioning Appliance, *American Journal of Orthodontics and Oral Surgery* (1945) 31:297-304.

Kesling, Coordinating the Predetermined Pattern and Tooth Positioner with Conventional Treatment, *Am. J. Orthod. Oral Surg.* (1946) 32:285-293.

Kleeman et al., The Speed Positioner, *J. Clin. Orthod.* (1996) 30:673-680.

Kunii et al., "Articulation Simulation for an Intelligent Dental Care System," *Displays* 15:181- 188 (1994).

Kuroda et al., Three-Dimensional Dental Cast Analyzing System Using Laser Scanning, *Am. J. Orthod. Dentofac. Orthop.* (1996) 110:365-369.

Laurendeau, et al., "A Computer-Vision Technique for the Acquisition and Processing of 3-D Profiles of Dental Imprints: An Application in Orthodontics," *IEEE Transactions on Medical Imaging*, 10(3):453-461 (Sep. 1991).

Leinfelder, et al., "A New Method for Generating Ceramic Restorations: a CAD-CAM System," *J. Am. Dent. Assoc.*, 118(6):703-707 (Jun. 1989).

Manetti, et al., "Computer-Aided Cefalometry and New Mechanics in Orthodontics," (Article Summary in English, article in German), *Fortschr. Kieferorthop.* 44, 370-376 (Nr. 5), 1983.

McCann, "Inside the ADA," *J. Amer. Dent. Assoc.*, 118:286-294 (Mar. 1989).

McNamara et al., "Invisible Retainers," *J. Clin. Orthod.*, pp. 570-578 (Aug. 1985).

McNamara et al., *Orthodontic and Orthopedic Treatment in the Mixed Dentition*, Needham Press, pp. 347-353 (Jan. 1993).

Moermann et al., "Computer Machined Adhesive Porcelain Inlays: Margin Adaptation after Fatigue Stress," IADR Abstract 339, *J. Dent. Res.*, 66(a):763 (1987).

Moles, "Correcting Mild Malalignments—As Easy As One, Two, Three," *AOA/Pro Corner*, vol. 11, No. 1, 2 pages (2002).

Mörmann et al., "Marginale Adaptation von adhäsuven Porzellaninlays in vitro," Separatdruck aus: Schweiz. Mschr. Zahnmed. 95: 1118-1129, 1985.

Nahoum, "The Vacuum Formed Dental Contour Appliance," *N. Y. State Dent. J.*, 30(9):385- 390 (Nov. 1964).

Nash, "CEREC CAD/CAM Inlays: Aesthetics and Durability in a Single Appointment," *Dent. Today*, 9(8):20, 22-23 (Oct. 1990).

Nishiyama et al., "A New Construction of Tooth Repositioner by LTV Vinyl Silicone Rubber," *J. Nihon Univ. Sch. Dent.*, 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," *Dentist*, 3 pages total, Jan./Feb. 1989.

Pinkham, "Inventor's CAD/CAM May Transform Dentistry," *Dentist*, 3 pages total, Sep. 1990.

Ponitz, "Invisible Retainers," *Am. J. Orthod.*, 59(3):266-272 (Mar. 1971).

Procera Research Projects, "PROCERA Research Projects 1993—Abstract Collection," pp. 3-28 (1993).

Proffit et al., *Contemporary Orthodontics*, (Second Ed.), Chapter 15, Mosby Inc., pp. 470-533 (Oct. 1993).

Raintree Essix & Ars Materials, Inc., Raintree Essix, Technical Magazine Table of contents and Essix Appliances, <httpz;//www.essix.com/magazine/default.html> Aug. 13, 1997, 7 pages.

Redmond et al., "Clinical Implications of Digital Orthodontics," *Am. J. Orthod. Dentofacial Orthop.*, 117(2):240-242 (2000).

Rekow et al., "CAD/CAM for Dental Restorations—Some of the Curious Challenges," *IEEE Trans. Biomed. Eng.*, 38(4):344-345 (Apr. 1991).

Rekow et al., "Comparison of Three Data Acquisition Techniques for 3-D Tooth Surface Mapping," *Annual International Conference of the IEEE Engineering in Medicine and Biology Society*, 13(1):344-345 (1991).

Rekow, "A Review of the Developments in Dental CAD/CAM Systems," (contains references to Japanese efforts and content of the papers of particular interest to the clinician are indicated with a one-line summary of their content in the bibliography), *Curr. Opin. Dent.*, 2:25-33 (Jun. 1992).

Rekow, "CAD/CAM in Dentistry: A Historical Perspective and View of the Future," *J. Can. Dent. Assoc.*, 58(4):283, 287-288 (Apr. 1992).

Rekow, "Computer-Aided Design and Manufacturing in Dentistry: A Review of the State of the Art," *J. Prosthet. Dent.*, 58(4):512-516 (Oct. 1987).

Rekow, "Dental CAD-CAM Systems: What is the State of the Art?", *J. Amer. Dent. Assoc.*, 122:43-48 (1991).

Rekow, "Feasibility of an Automated System for Production of Dental Restorations, Ph.D. Thesis," Univ. of Minnesota, 244 pages total, Nov. 1988.

Richmond et al., "The Development of the PAR Index (Peer Assessment Rating): Reliability and Validity," *Eur. J. Orthod.*, 14:125-139 (1992).

Richmond et al., "The Development of a 3D Cast Analysis System," *Br. J. Orthod.*, 13(1):53- 54 (Jan. 1986).

Richmond, "Recording The Dental Cast in Three Dimensions," *Am. J. Orthod. Dentofacial Orthop.*, 92(3):199-206 (Sep. 1987).

Rudge, "Dental Arch Analysis: Arch Form, A Review of the Literature," *Eur. J. Orthod.*, 3(4):279-284 (1981).

Sakuda et al., "Integrated Information-Processing System in Clinical Orthodontics: An Approach with Use of a Computer Network System," *Am. J. Orthod. Dentofacial Orthop.*, 101(3): 210-220 (Mar. 1992).

Schellhas et al., "Three-Dimensional Computed Tomography in Maxillofacial Surgical Planning," *Arch. Otolamgol. Head Neck Surg.*, 114:438-442 (Apr. 1988).

Schroeder et al., Eds. *The Visual Toolkit*, Prentice Hall PTR, New Jersey (1998) Chapters 6, 8 & 9, (pp. 153-210,309-354, and 355-428, respectively).

Shilliday, (1971). Minimizing finishing problems with the minipositioner, *Am. J. Orthod.* 59:596-599.

Siemens, "CEREC—Computer-Reconstruction," High Tech in der Zahnmedizin, 14 pages total.

Sinclair, "The Readers' Corner," *J. Clin. Orthod.*, 26(6):369-372 (Jun. 1992).

Sirona Dental Systems GmbH, *CEREC 3D, Manuel utiiisateur*, Version 2.0X (in French), 2003,114 pages total.

(56) References Cited

OTHER PUBLICATIONS

Stoll et al., "Computer-aided Technologies in Dentistry," (article summary in English, article in German), *Dtsch Zahna'rztl Z* 45, pp. 314-322 (1990).

Sturman, "Interactive Keyframe Animation of 3-D Articulated Models," Proceedings Graphics Interface '84, May-Jun. 1984, pp. 35-40.

Truax L., "Truax Clasp-Less(TM) Appliance System," *Funct. Orthod.*, 9(5):22-4, 26-8 (Sep.-Oct. 1992).

Tru-Tain Orthodontic & Dental Supplies, Product Brochure, Rochester, Minnesota 55902, 16 pages total.

U.S. Department of Commerce, National Technical Information Service, "Automated Crown Replication Using Solid Photography SM," Solid Photography Inc., Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed on Jun. 20, 1997, 41 pages total.

Van Der Linden et al., "Three-Dimensional Analysis of Dental Casts by Means of the Optocom," *J. Dent. Res.*, p. 1100 (Jul.-Aug. 1972).

Van Der Linden, "A New Method to Determine Tooth Positions and Dental Arch Dimensions," *J. Dent. Res.*, 51(4):1104 (Jul.-Aug. 1972).

Van Der Zel, "Ceramic-Fused-to-Metal Restorations with a New CAD/CAM System," *Quintessence Int.*, 24(11):769-778 (1993).

Varady et al., "Reverse Engineering of Geometric Models—An Introduction," *Computer—Aided Design*, 29(4):255-268, 1997.

Verstreken et al., "An Image-Guided Planning System for Endosseous Oral Implants," *IEEE Trans. Med. Imaging*, 17(5):842-852 (Oct. 1998).

Warunek et al., Physical and Mechanical Properties of Elastomers in Orthodonic Positioners, *Am J. Orthod. Dentofac. Orthop*, vol. 95, No. 5, (May 1989) pp. 399-400.

Wells, Application of the Positioner Appliance in Orthodontic Treatment, *Am. J. Orthodont.* (1970) 58:351-366.

Williams, "Dentistry and CAD/CAM: Another French Revolution," *J. Dent. Practice Admin.*, pp. 2-5 (Jan./Mar. 1987).

Williams, "The Switzerland and Minnesota Developments in CAD/CAM," *J. Dent. Practice Admin.*, pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL <http://wscg.zcu.cz/wscg98/wscg98.h>.

Xia et al., "Three-Dimensional Virtual-Reality Surgical Planning and Soft-Tissue Prediction for Orthognathic Surgery," *IEEE Trans. Inf. Technol. Biomed.*, 5(2):97-107 (Jun. 2001).

Yamamoto et al., "Optical Measurement of Dental Cast Profile and Application to Analysis of Three-Dimensional Tooth Movement in Orthodontics," *Front. Med. Biol. Eng.*, 1(2):119-130 (1988).

Yamamoto et al., "Three-Dimensional Measurement of Dental Cast Profiles and Its Applications to Orthodontics," *Conf. Proc. IEEE Eng. Med Biol. Soc.*, 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," *Nippon Dental Review*, 452:61-74 (Jun. 1980).

Yoshii, "Research on a New Orthodontic Appliance: The Dynamic Positioner (D.P.); II. The D.P. Manufacturing Procedure and Clinical Applications," *Nippon Dental Review*, 454:107-130 (Aug. 1980).

Yoshii, "Research on a New Orthodontic Appliance: The Dynamic Positioner (D.P.); III.—The General Concept of the D.P. Method and Its Therapeutic Effect, Part 2, Skeletal Reversed Occlusion Case Reports," *Nippon Dental Review*, 458:112-129 (Dec. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," *Nippon Dental Review*, 457:146-164 (Nov. 1980).

\* cited by examiner

FIG. 9A
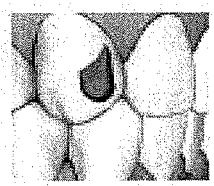
FIG. 9B
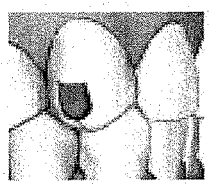
FIG. 9C
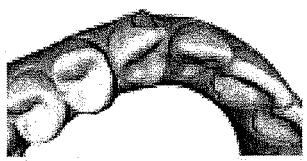
FIG. 9D
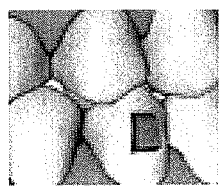
FIG. 9E
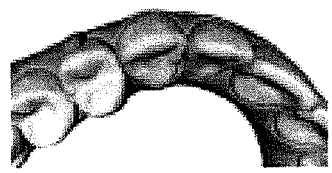
FIG. 9F
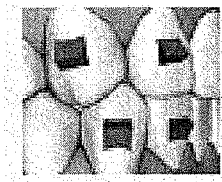
FIG. 9G
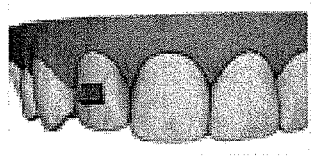
FIG. 9H
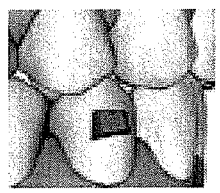
FIG. 9I
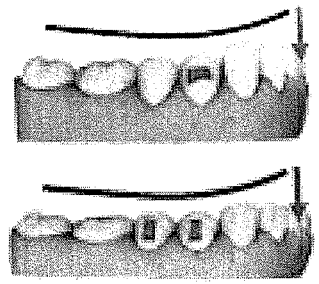
FIG. 9J

G. 15D

ORTHODONTIC SYSTEMS AND METHODS INCLUDING PARAMETRIC ATTACHMENTS

CROSS-REFERENCES TO RELATED APPLICATIONS

The present application claims the benefit of priority under 35 U.S.C. §119(e) of U.S. Application No. 61/116,448, filed Nov. 20, 2008 and U.S. Application No. 61/242,379, filed Sep. 14, 2009, the entire contents of which are incorporated herein by reference.

BACKGROUND OF THE INVENTION

The present invention relates generally to the field of orthodontics, and more particularly to tooth attachments for engaging a dental repositioning appliance, the attachments having improved or optimized design parameters and/or geometries customized to the individual patient and/or for improved application of a desired force system selected to elicit the identified tooth movement.

An objective of orthodontics is to move a patient's teeth to positions where function and/or aesthetics are optimized. Traditionally, appliances such as braces are applied to a patient's teeth by an orthodontist or dentist and the set of braces exerts continual force on the teeth and gradually urges them toward their intended positions. Over time and with a series of clinical visits and adjustments to the braces, the orthodontist adjusts the appliances to move the teeth toward their final destination.

More recently, alternatives to conventional orthodontic treatment with traditional affixed appliances (e.g., braces) have become available. For example, systems including a series of preformed aligners have become commercially available from Align Technology, Inc., Santa Clara, Calif., under the tradename Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as software technology available from Align Technology, Inc. The design of the aligners can rely on computer modeling of a series of planned successive tooth arrangements, and the individual aligners are designed to be worn over the teeth and elastically reposition the teeth to each of the planned tooth arrangements.

Orthodontic appliances and systems often make use of tooth attachments or components bonded on a surface of a tooth in order to elicit a desired tooth movement. Appliances, in general, apply force and/or torque on a tooth crown to move teeth, with the applied force typically normal with respect to the surface of a tooth or attachment positioned on the tooth. Currently, orthodontic systems typically use a number of generic or standard attachments to accomplish orthodontic tooth movement. A tooth movement may be identified, and then a generic or standard attachment is selected for use in connection with a repositioning appliance. Selection and positioning of the attachment is typically accomplished based on clinical experience or at the discretion of the treating professional. Unfortunately, such current approaches have proven in some cases to be of limited success as the selected attachment configurations and/or positioning on the tooth may fail to deliver optimal or even sufficient application of forces so as to elicit the desired tooth movement. In some instances, actual forces applied to the teeth are not as initially expected, and may result in lack of movement or incorrect and unwanted tooth movement. Current tooth attachments used for rotation have the same shape and position for all patients and teeth undergoing movement with a rotation component. Due to the individual morphology of teeth and composite movements, the performance of such attachments may not be optimal for all patients.

Accordingly, improved techniques and orthodontic systems are needed for designing and providing more effective tooth movement forces to the teeth during orthodontic treatment using tooth attachments, and reducing unwanted tooth movements.

BRIEF SUMMARY OF THE INVENTION

The present invention provides orthodontic systems and related methods for designing and providing improved or more effective tooth moving systems for eliciting a desired tooth movement and/or repositioning teeth into a desired arrangement. Methods and orthodontic systems of the invention include tooth attachments having improved or optimized parameters selected or modified for more optimal and/or effective application of forces for a desired/selected orthodontic movement. Attachments of the present invention can be customized to a particular patient (e.g., patient-customized), a particular movement, and/or a sub-group or sub-set of patients, and configured to engage an orthodontic tooth positioning appliance worn by a patient, where engagement between the attachment and orthodontic appliance results in application of a repositioning force or series/system of forces to the tooth having the attachment and will generally elicit a tooth movement.

In one aspect, the present invention is directed to a computer implemented method for designing a tooth movement system for eliciting a selected movement of a patient's tooth. The method includes receiving a digital model of the patient's tooth. A desired force system for eliciting the selected tooth movement is determined. A patient-customized attachment is then designed. The attachment is configured to engage an orthodontic appliance when worn by a patient and apply a repositioning force to a tooth corresponding to the selected force system. The attachment includes one or more parameters having values selected based on the digital model, the selected force system, and one or more patient-specific characteristics, thereby providing improved application of the selected force system to the patient's tooth.

In another aspect, the present invention is directed to a method for generating a tooth movement system including a tooth attachment configured to engage an orthodontic appliance worn by a patient and apply a repositioning force system to a tooth corresponding to a selected movement of the patient's tooth. The method includes determining a desired force system to be applied to the patient's tooth so as to elicit the selected tooth movement. A first attachment is selected from a group of non-custom attachments. A first force system that is applied to a tooth having the first attachment and engaged with an orthodontic appliance is modeled. An optimized attachment is then generated by modifying one or more parameter values of the first attachment such that a second force system applied to the tooth having the optimized attachment and engaged with an orthodontic appliance worn by the patient more closely corresponds to the desired force system than the first force system.

In another aspect, the present invention is directed to an orthodontic system for delivery of a tooth movement force to a patient's tooth. The orthodontic system includes a patient customized orthodontic attachment. The patient customized orthodontic attachment is configured to engage an orthodontic appliance when worn by a patient and apply a repositioning force system to a tooth corresponding to a selected force system. The attachment includes one or more parameters having values modified or selected based on the selected force system and one or more patient-specific characteristics.

In another aspect, the present invention is directed to a method for designing a tooth movement system comprising one or more tooth attachments for eliciting a selected movement of a patient's tooth. The method includes determining force or torque values of a desired force system for eliciting the selected tooth movement. A movement optimized or patient-customized attachment is designed. The attachment is configured to engage an orthodontic appliance when worn by a patient and apply a repositioning force to the tooth. The attachment includes one or more parameter values modified based on the determined force or torque values such that the applied repositioning force substantially matches the desired force system.

In another aspect, the present invention is directed to a method for designing a tooth movement system. The method includes identifying a range of force or torque values corresponding to a desired force system to be applied to a tooth so as to elicit a selected tooth movement. A first force or torque value applied to a tooth is modeled when a first attachment disposed on the tooth is engaged with an orthodontic appliance. The first attachment has parameters affecting the force or torque applied to the tooth during engagement. The first force or torque value is identified as being within the range of values. An optimized attachment is then generated by modifying one or more parameter values of the first attachment such that a second force or torque is applied to a tooth having the optimized attachment and engaged with an orthodontic positioning appliance. The second force or torque value is higher or lower in the range of values compared to the first force system and selected to optimize force/torque application to a tooth during orthodontic treatment.

In another aspect, the present invention is directed to a method for designing an attachment for eliciting a selected movement of a patient's tooth. The method includes identifying an initial position of an attachment on a tooth at a location on a digital model of the patient's dentition. Attachment parameters are computed based on the initial position of the attachment and a geometry of the tooth. Each attachment parameter is associated with a predetermined range of values corresponding to optimal force or optimal torque for the selected movement of the tooth. In the event that at least one value of the computed parameters is not within the predetermined range of values, at least one of the attachment parameters and the position of the attachment on the tooth is modified such that all of the attachment parameters are within the predetermined range of values.

BRIEF DESCRIPTION OF THE DRAWINGS

FIGS. 9A through 9L illustrate exemplary attachments according to various embodiments of the present invention.

FIGS. 15C-15D illustrate a relief addition to the dental appliance to counteract the undesirable force vector around the tooth, and the resulting desired application of the predetermined force on the tooth by the dental appliance, respectively.

DETAILED DESCRIPTION OF THE INVENTION

The present invention provides orthodontic systems and related methods for designing and providing improved or more effective tooth moving systems for eliciting a desired tooth movement and/or repositioning teeth into a desired arrangement. Methods and orthodontic systems of the invention include tooth attachments having improved or optimized parameters selected or modified for more optimal and/or effective application of forces for a desired/selected orthodontic movement. Attachments of the present invention can be customized to a particular patient (e.g., patient-customized), a particular movement, and/or a sub-group or sub-set of patients, and configured to engage an orthodontic tooth positioning appliance worn by a patient, where engagement between the attachment and orthodontic appliance results in application of a repositioning force or series/system of forces to the tooth having the attachment and will generally elicit a tooth movement.

Figures 1A, 1B:
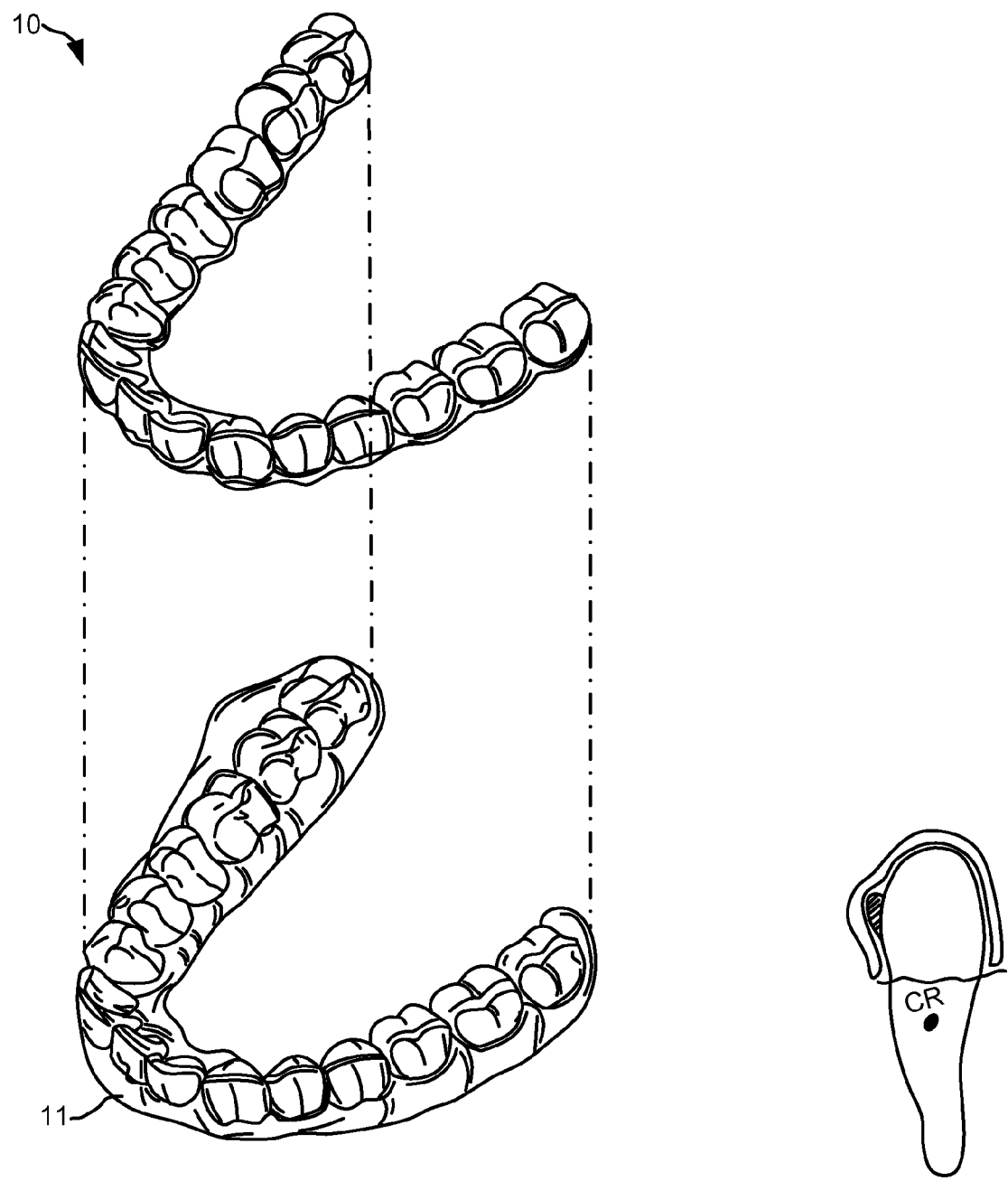
FIG. 1A illustrates a jaw together with an incremental positioning adjustment appliance according to an embodiment of the present invention.
FIG. 1B shows a cross-sectional diagram of an appliance engaging a tooth crown and positioned attachment.

Orthodontic systems of the present invention can include tooth attachments and one or more orthodontic appliances that engage the attachments when worn by a patient. Appliances having teeth receiving cavities that receive and reposition teeth, e.g., via application of force due to appliance resiliency, are generally illustrated with regard to FIG. 1A. As illustrated, FIG. 1A shows one exemplary adjustment appliance 10 which is worn by the patient in order to achieve an incremental repositioning of individual teeth in the jaw 11. The appliance can include a shell (e.g., polymeric shell) having teeth-receiving cavities that receive and resiliently reposition the teeth. Similar appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com"). Appliances according to the present invention can be designed to engage one or more attachments positioned on a tooth of the patient, as further described below. As further described herein, tooth attachments can be designed, oriented, and/or located on a patient's tooth to precisely control the moments produced on a patient's tooth as the appliance is worn by the patient. Customized design and use in orthodontic treatment as described herein can advantageously improve effectiveness of treatment and clinical results by more precisely applying force vectors of necessary magnitude and direction for desired movement. Orthodontic systems of the present invention including appliances and tooth attachments as described further provide an efficient force distribution mechanism that can more effectively reduce unwanted force and moment.

A tooth attachment for delivering a movement force or system of forces is further illustrated with reference to FIG. 1B. The attachment is coupled to a surface of the tooth on the tooth crown and can couple with or engage a dental appliance or aligner as illustrated in FIG. 1A when the appliance is worn by the patient. When worn by the patient, the appliance engages the tooth crown and attachment, with interaction/contact between an activator, e.g., one or more surfaces or portions of the internal cavity of the appliance, and corresponding surfaces/portions of the tooth attachment and/or tooth crown to apply a system of forces for eliciting tooth movement. Various tooth movements can be accomplished, as further noted below.

As set forth in the prior applications, an appliance can be designed and/or provided as part of a set or plurality of appliances and treatment can be administered according to a treatment plan. In such an embodiment, each appliance may be configured so that one or more tooth-receiving cavities has a geometry corresponding to an intermediate or final tooth arrangement intended for the appliance. Appliance geometries can be further designed or modified (e.g., modified to accommodate or operate in conjunction with tooth attachments) so as to apply a desired force or system of forces to the patient's teeth and elicit a desired tooth movement and gradually reposition teeth to an intended arrangement. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance until the pressure of each appliance on the teeth can no longer be felt. A plurality of different appliances (e.g., set) can be designed and even fabricated prior to the patient wearing any appliance of the plurality. At that point, the patient replaces the current adjustment appliance with the next adjustment appliance in the series until no more appliances remain. The appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Orthodontic appliances, such as illustrated in FIG. 1A, impart forces to the crown of a tooth and/or an attachment positioned on the tooth at each point of contact between a tooth receiving cavity of the appliance and received tooth and/or attachment. The magnitude of each of these forces and their distribution on the surface of the tooth determines the type of orthodontic tooth movement which results. Types of tooth movements are conventionally delineated as extrusion, intrusion, rotation, tipping, translation and root movement. Tooth movement of the crown greater than the movement of the root is referred to as tipping. Equivalent movement of the crown and root is referred to as translation. Movement of the root greater than the crown is referred to as root movement.

For illustrative purposes, three types of tooth movement can be identified as divisions of a continuum of possible movements. Tooth movements may be in any direction in any plane of space. The present disclosure uses the orthodontic convention of delineating movements in three dimensional space into three classifications: first order, second order and third order.

The magnitudes of the forces selected and applied to the teeth, and the proper selection of the locations and distributions on the tooth surface upon which they act, are important to controlling the type of tooth movement which is achieved. Previously existing attachment technology does not provide for customizing attachments to an individual patient or the specific tooth movement desired, or optimizing or precisely controlling the forces (e.g., collection or system of forces) applied to a patient's tooth to elicit a desired movement of the tooth.

Figure 2A:
FIG. 2A provides a flow diagram illustrating a conventional approach to orthodontic attachment methodologies.

Existing orthodontic systems and methods utilizing attachments typically make use of a limited number of generic or standard attachments to accomplish orthodontic tooth movement. According to previously existing approaches, a generic or standard attachment used may be selected based on the type of tooth movement that is required, with no predictive or force-modeling inquiry (see, e.g., FIG. 2A). For example, orthodontic knowledge or clinical practice may lead an orthodontic practitioner to select a particular attachment from a group of existing generic attachments where the attachment is known or expected to be more well suited for the desired tooth movement. However, such particular selection is limited in terms of patient or tooth movement tailored treatment, e.g., due to the limited number of choices, and differs from the "customization" of attachment design described herein. More typically and in many treatment approaches, a single or same general attachment design/configuration is used for the same movement on all teeth on all patients; a "one size fits all" approach. While the selection of an attachment to be used for a movement was conventionally based on general guidelines of clinical experience or based on the discretion of a treating professional, little optimization/customization of selected attachment to a force system required to elicit a desired movement was performed, and the actual force system that would be accomplished by a selected attachment and position was evaluated following use, e.g., by observation of clinical results.

Figure 2B:
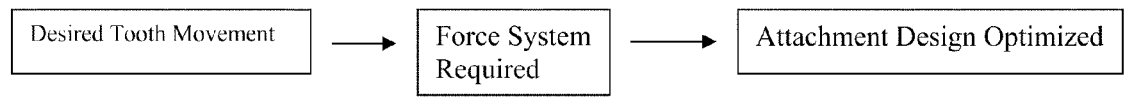
FIG. 2B provides a flow diagram illustrating orthodontic attachment selection/design methodologies, according to an embodiment of the present invention.

As such, previous approaches to tooth movement by use of dental attachments has proven to have shortcomings in some instances in that they do not optimally incorporate the principles of biomechanics, force modeling, and/or predictive modeling into the design of the attachment. Therefore, the resulting uncertainty of the actual movement forces imparted by a generic or non-customized attachment can sometimes lead to inadequate and/or improper force systems applied to the tooth, which can result in incorrect and unwanted tooth movement. The present invention advantageously provides that for a given desired movement of a tooth, various attachment parameters such as attachment geometry and positioning of the attachment are optimized for the desired/specified movement. This optimization process is based not only on the desired tooth movement, but can incorporate principles of biomechanics, biomechanical and force testing and/or modeling, and the characteristics of the specific tooth to be moved in determining the characteristics of the attachment. Further customization can be accomplished based on characteristics of the specific tooth of the individual patient to be moved. FIG. 2B illustrates generally a process of attachment design optimization. Attachment design customization can further be accomplished with incorporation or consideration of characteristics of the individual patient's (or group of patients) tooth, such as tooth size, width, contour, length, long axis, and the like. As illustrated in FIG. 2B, the present invention can include identifying the desired tooth movement, determining the force system or series of applied forces required to elicit the desired tooth movement, and designing an attachment optimized to deliver the identified force system or substantially similar force system to the patient's tooth for the desired tooth movement. As further set forth herein, attachment design and optimization may include modeling or predicting a force system applied to the tooth with use of a selected attachment, and may include further modification or adjustment of one or more attachment parameters. In one embodiment, a method may include first selecting an attachment design, and then determining the force system applied to the tooth by orthodontic use of the attachment, and further determining whether the predicted force system is suitable for eliciting the desired tooth movement.

Attachment parameters having values that can be selected/modified according to the present invention include any parameter or feature of an attachment that, if modified, effects a force or torque applied to a patient's tooth, on which it is disposed, during orthodontic treatment. Generally speaking, non-limiting examples of attachment parameters can include or relate to attachment, in whole or in part, geometry, shape, sizing, composition, positioning, and the like. Attachment parameter values can be selected or modified for optimization (e.g., selected movement optimization) and/or patient customization. Patient customization refers to the selection or modification of an attachment parameter value in response to a specific feature or characteristic of an individual patient being treated or, in some cases, a specific and generally limited class of patients. Various patient characteristics can be included and considered according to the present invention and will include any characteristic of a patient that can effect tooth movement or orthodontic treatment. Non-limiting patient specific characteristics include teeth shapes, morphology features, teeth or surface orientation, relationship of teeth to one another and to other parts of the masticatory system, root characteristics, treatment planning considerations, such as tooth movement paths, collisions, etc. Patient characteristics may further include more general characteristics such as age, gender, race, various lifestyle considerations, nutrition, dental hygiene, and the like.

In one aspect, the present invention provides improved attachments as well as methods for determining the parameters (e.g., geometric parameters) of these attachments and values for these parameters that provide for improved control of the force system delivered to the tooth by the attachment. Application of correct and appropriate force systems to a tooth results in precise controlled orthodontic tooth movement and is considered an improvement in orthodontic treatment. Treatment goals can be more successfully achieved and shorter treatment times attained leading to increased patient satisfaction. In one embodiment, an inventive method optimizes an attachment design which considers the location and orientation of the surface(s) of the attachment as required to accomplish a desired movement of a specific tooth.

As noted above, appliances or aligners accomplish tooth movement by applying a series or system of forces (force system) comprised of forces, the moment of a force, and the moment of a couple to a tooth to elicit a biological response of the periodontal tissues and bone structures which surround the tooth. Different force systems result in different types of tooth movement: tipping, translation, root movement, etc. In some cases, the aligner alone cannot deliver the force system required to accomplish a desired tooth movement. An amount of material or structure, commonly referred to in the orthodontic arena as an attachment, can be bonded to the tooth to aid the aligner in delivering the appropriate force system to the tooth. The state-of-the-art in attachments is fixed geometric shapes which are indicated for use when a specific tooth movement is desired. However, the selection of an attachment paired with the aligner to improve movement has historically been determined from clinical observation alone and has demonstrated in some instances limited clinical success and lack of precise clinical control of the force system deliverer to the tooth. Methods and systems according to the present invention advantageously consider and account for various factors which can have a significant effect on imparting a precise force system to a tooth, including biomechanical principles, tooth morphology, attachment location, attachment orientation, and probability of engagement between the aligner. The present invention uses these inputs to determine the optimal design of the attachment to be used with the aligner for the specific movement of a specific tooth, and accommodate specific attachment characteristics determined for a specific tooth and specific desired movement. Thus, the current attachments and orthodontic systems provide optimized as well as customized individualized attachment design for a specific tooth and a specific movement.

Figure 2C:
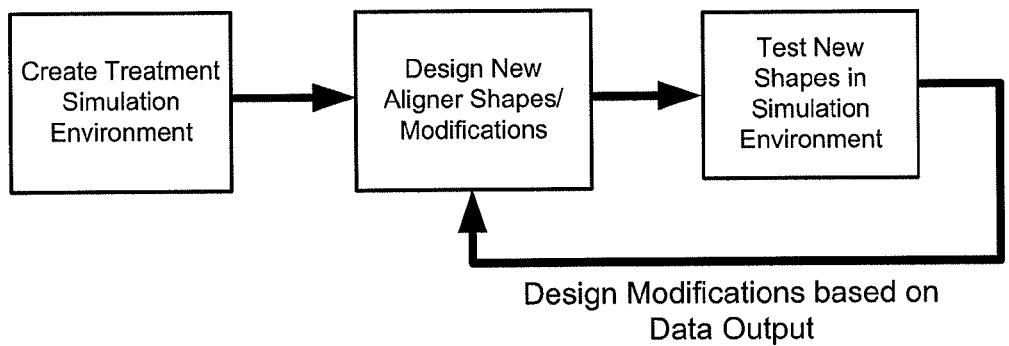
FIG. 2C provides a flow diagram illustrating an attachment optimization process, according to an embodiment of the present invention.

FIG. 2C illustrates an attachment optimization process, according to an embodiment of the present invention. The process includes providing or creating a treatment or force application simulation environment. A simulation environment can include, e.g., computer modeling systems, biomechanical systems or apparatus, and the like. One or more aligner shapes or candidate attachment designs can be selected for testing or force modeling. As noted above, a desired tooth movement, as well as a force system required or desired for eliciting the desired tooth movement can be identified. Using the simulation environment, a candidate attachment shape(s) can be analyzed or modeled for determination of an actual force system resulting from use of the candidate attachment. One or more modifications can optionally be made to a candidate attachment, and force modeling can be further analyzed as described.

Figure 2D:
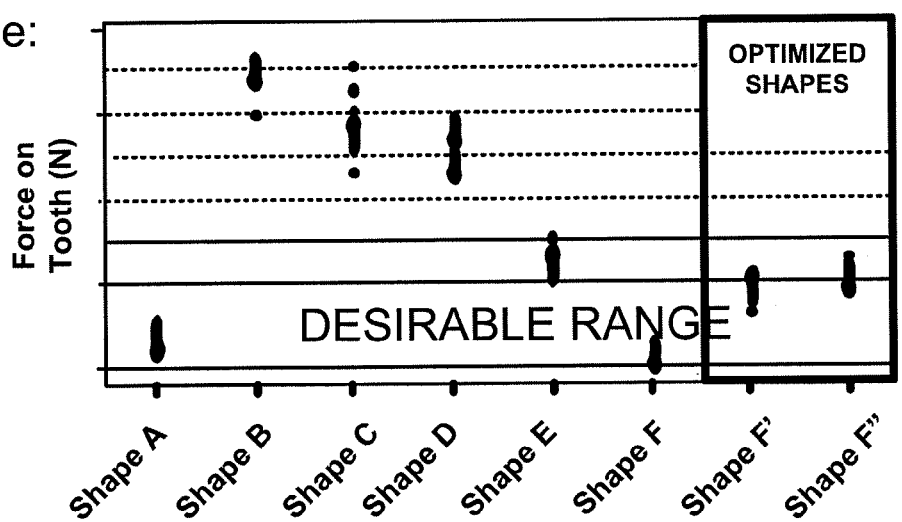
FIG. 2D illustrates attachment design optimization according to an embodiment of the present invention.

FIG. 2D illustrates attachment force modeling and design optimization, according to an embodiment of the present invention. As above, a desired tooth movement and a force system required or desired (or value range of tooth movement force or torque) for eliciting the desired tooth movement can be identified. One or more attachment designs (e.g., Shapes A-F) can be selected for analysis of a corresponding force system applied, with identification of attachment designs having tooth movement force application falling within an identified or desired range. Attachment designs can further be modified, e.g., modification of one or more attachment parameter values, for modification or further optimization for application of the desired force system.

In one embodiment, an attachment may be identified as having a force or torque value falling outside the identified range, and generating an optimized attachment can include modifying one or more parameter values of the attachment so as to bring the force or torque value of the attachment within the identified range. In another embodiment, a method may include identification of an attachment with a force/torque falling within the desired range, followed by modification of parameter value(s) accomplished such that the force/torque of the modified or optimized attachment fall within a different portion of the desired range. For example, an attachment may be identified as having force/torque values in a lower portion of a desired range, with modifications selected to optimized the attachment so as to provide force/torque values higher within the desired range. See, e.g., FIG. 2D, Shape F compared to Shape F' and F".

A method of designing a tooth movement system including one or more optimized and/or customized attachments for eliciting a desired movement of a patient's tooth, according to the present invention is described with reference to FIG. 3. A desired tooth movement can be identified for orthodontic treatment. Biomechanical principles, modeling techniques, force calculation/measurement techniques, and the like, including knowledge and approaches commonly used in orthodontia may define the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc., including methods further described herein. The result of the determination is a desired force system to be applied to the tooth. An initial attachment geometry can be assumed and described by a group of parameters. The force system produced by this initial geometry may then be determined by computer modeling or measured directly. The force system may be defined with respect to a reference point, such as an axis of the tooth or any dental characteristic. The tooth morphology and surface orientation may be taken into account when determining the attachment design. The surface of the tooth may have an orientation such that when a generic attachment shape is bonded to the surface of the tooth, the force is not correctly directed. The surface orientation(s) of the parametric attachment is then altered to compensate for the tooth surface orientation and the force is redirected in a more favorable direction. Location of the attachment on the tooth may be altered as well to determine the position which produces the optimal force system. Orientation such as rotation around an axis or linear movement may be altered as well to optimize the force system. Each parameter of consequence in determining the force system produced by the attachment may then be incremented within clinically relevant values and the optimal design identified.

Figure 3:
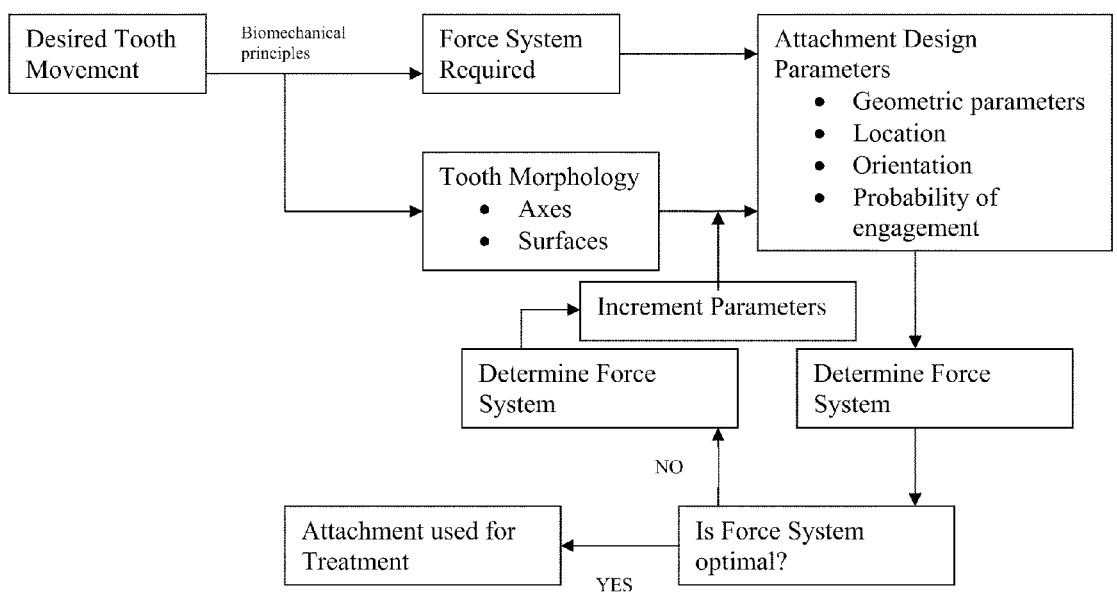
FIG. 3 provides a logical flow diagram illustrating orthodontic selection/design methodology according to an embodiment of the present invention.

FIG. 3 illustrates a logical flow diagram illustrating an orthodontic selection/design methodology embodiment for attachment optimization and/or customization of the present invention.

Parameters which define attachments and may have their values incremented to determine the combinations which produce the desired force system include surface area, surface orientation, location on the tooth, size (length, depth, height), prominence defined as the distance an attachment is out of the tooth surface. Parameters which define the attachment geometry, orientation and location may be referenced with respect to the tooth or any anatomical structure or any reference defined from these. Attachment parameters may be defined, e.g., with respect to the FACC axis (facial axis of the clinical crown), one or more axes of the tooth, any reference plane including those of the tooth, the occlusion, the skeleton or the soft tissue. Parameters of the attachment may defined with respect to any axis of a multiple rooted tooth.

For attachments comprised of curved portions, parameters defining the attachment's location and orientation may include in addition to those indicated above curvatures, arcs, radii, tangential directions, major and minor axes or any other characteristic used in defining the overall shape. Desired movements may be defined in 2D space when appropriate and designated by common orthodontic terminology such as first, second or third order, extrusion, intrusion, rotation, inclination, in-out, tipping, torque, etc. Dental movements within the plane of the arch are described as first order. Rotation about an axis perpendicular to the occlusal plane is an example. Dental movements along the arch are described as second order. Mesio-distal root tip is an example of a second order movement. Dental movements about the arch are described as third order. Anterior root torque is an example of a third order movement.

Figure 4:
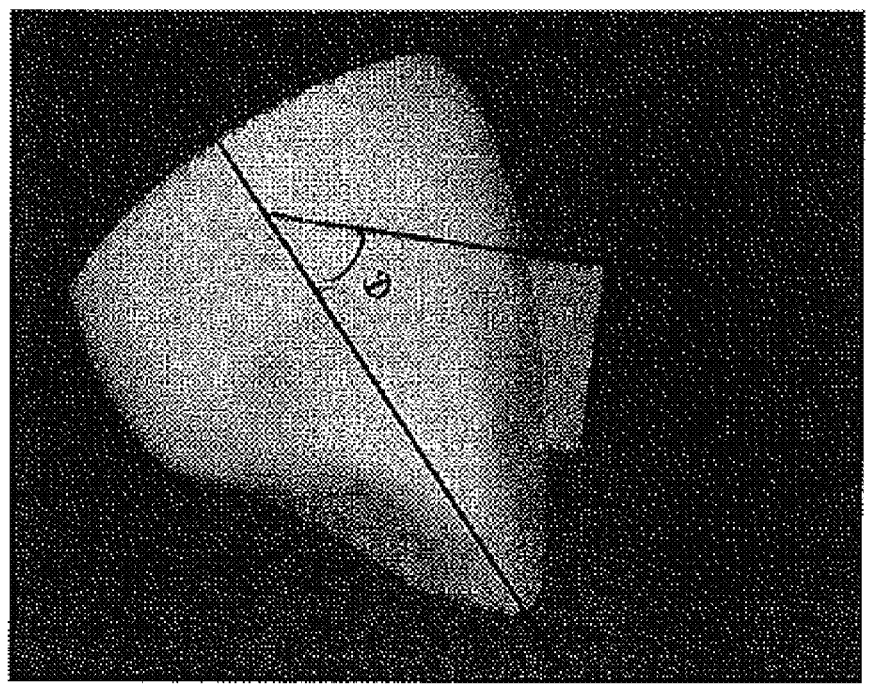
FIG. 4 illustrates an attachment having one or more parameters identified with respect to a tooth axis, according to an embodiment of the present invention.

In one embodiment shown in FIG. 4, the desired/selected 2D movement is extrusion and the parameter of the attachment to optimize the force system is referenced with respect to the long axis of the tooth. The desired force system is determined to be a force parallel to the long axis of the tooth. A rectangular attachment placed at the FACC point on the clinical crown does not produce the optimal force system. The disclosed invention determines the parameter of the attachment to vary to compensate for the variation in angle between the long axis and the direction of the surface of the tooth onto which the attachment is bonded. The orientation of one facade of the attachment which optimizes or improves the force system is shown with respect to the long axis. The disclosed invention includes determination of the parameter to vary to compensate for the tooth surface morphology when optimizing or improving the force system.

Figure 5:
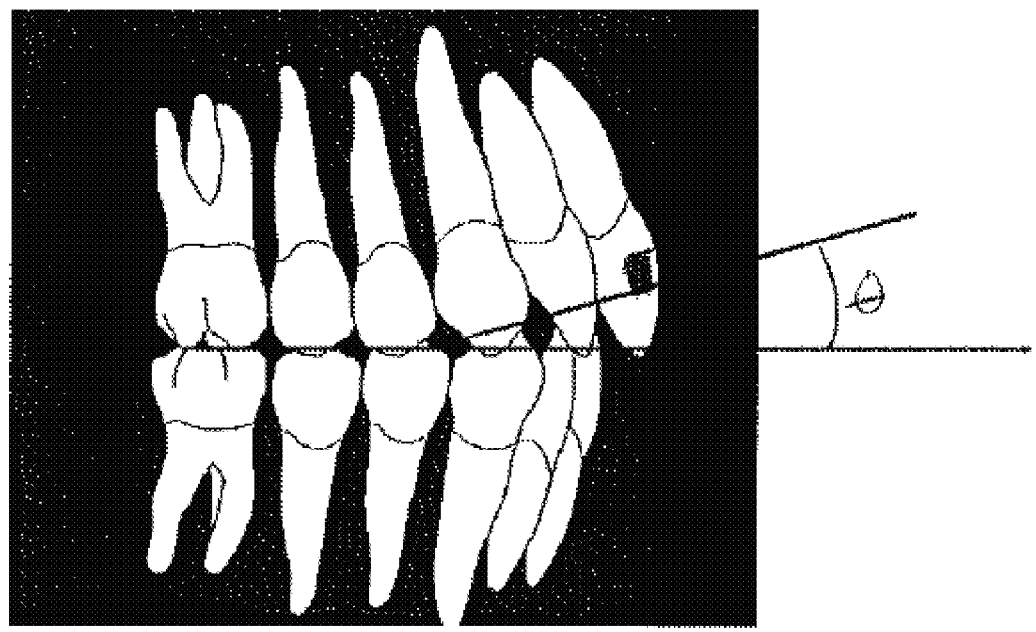
FIG. 5 illustrates an attachment having one or more parameters identified with respect to an occlusal plane of the dentition, according to an embodiment of the present invention.
Figure 6:
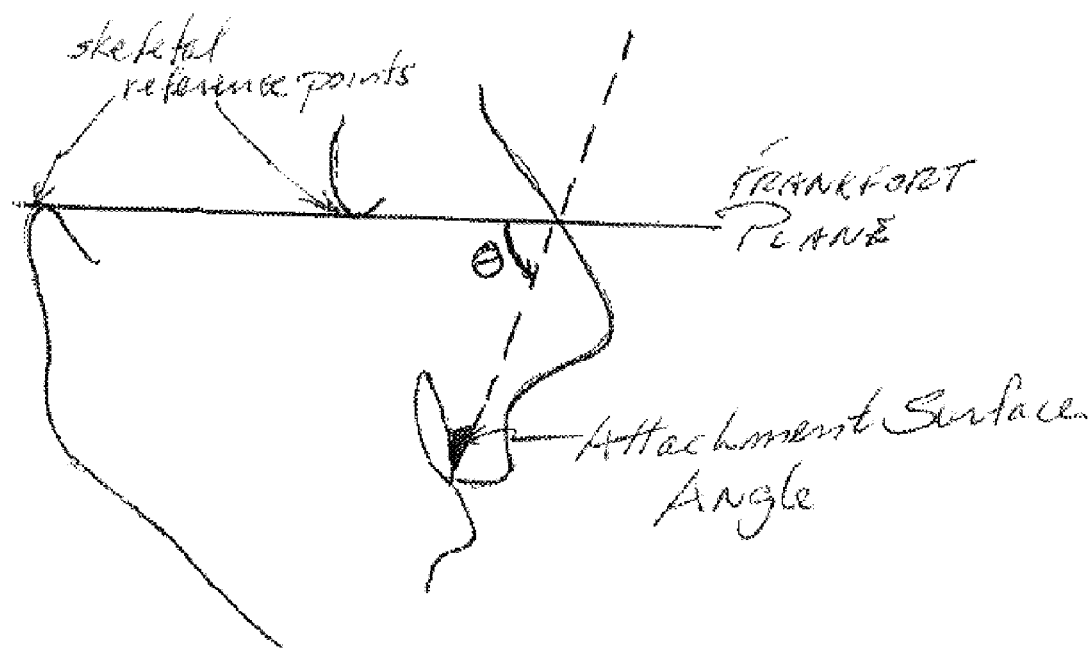
FIG. 6 illustrates an attachment having one or more parameters identified with respect to an anatomical or skeletal feature of the patient, according to an embodiment of the present invention.
Figure 7:
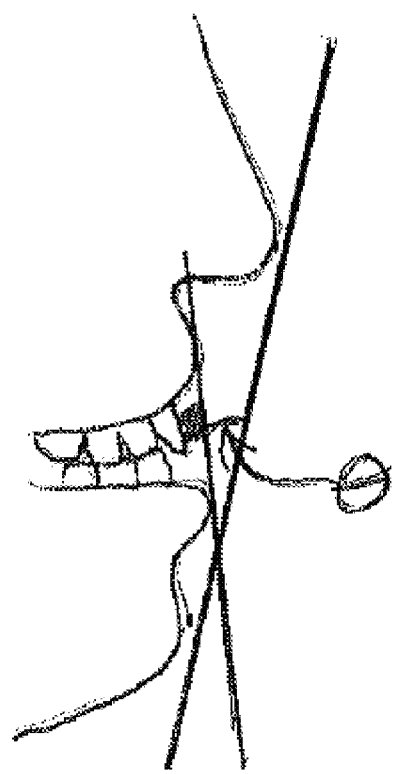
FIG. 7 illustrates an attachment having one or more parameters identified with respect to a soft tissue feature or aspect of the patient, according to an embodiment of the present invention.

Desired tooth movements, forces, as well as attachment parameters may be defined with respect to various anatomical features. As illustrated in FIG. 5, for example, the parameter is defined with respect to the occlusal plane of the dentition. As illustrated in FIG. 6, for example, the parameter is defined with respect to a feature of the skeleton. As illustrated in FIG. 7, for example, the parameter is defined with respect to an aspect or feature of the soft tissue of the patient.

An additional advantage of the disclosed invention is that a customized or optimized attachment may be designed less sensitive to clinical error, that is, a "more forgiving" attachment in which the force system does not vary substantially when location or fabrication accuracy is compromised. Further, one or more parameters may be incrementally varied. Variation of a parameter over a range of values which results in the least effect on the desired force system (or a specific component of the force system) allows for the greatest variation or inaccuracies during use.

Another advantage of the present invention includes optimizing or improving probability of desired engagement between an attachment and an appliance. Appliances or aligners typically do not engage (e.g., contact) all attachment shapes well. An attachment design optimized according to the present invention engages the aligner in a reproducible way, that is, minimal or no variation in engagement is produced upon multiple insertions of an aligner onto an attachment. Thus, multiple attachment/aligner engagements will result in substantially the same force system being produced. Such reproducible engagement can advantageously provide a more effective tooth movement being attained. Improved or optimal designs are determined by the means described in the previous paragraph.

Figure 8:
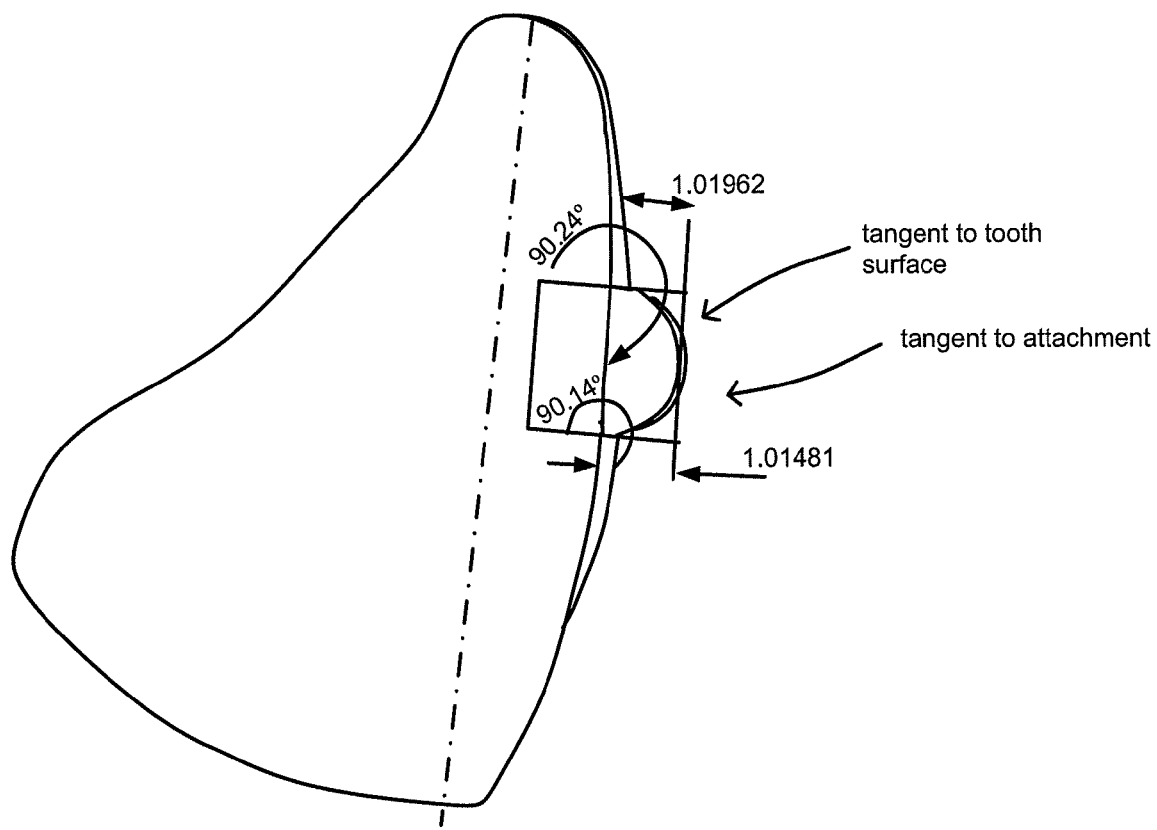
FIG. 8 illustrates an attachment having arcs and radii, according to an embodiment of the present invention.
Figure 9K:
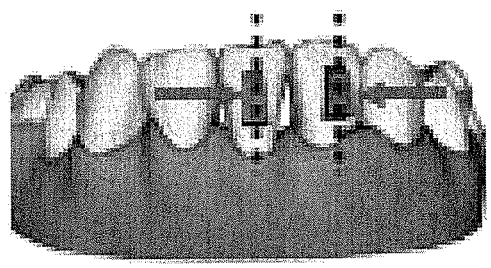
Figure 9L:

FIG. 8 illustrates an attachment having arcs and radii. FIGS. 9A through 9L illustrate exemplary tooth attachments. FIGS. 9A through 9C illustrate attachments optimized for tooth rotational movements (e.g., cuspid rotation). FIGS. 9D and 9E illustrate an attachment selected and positioned for a tooth rotation movement (e.g., bicuspid rotation). FIGS. 9F and 9G illustrate attachments (e.g., beveled gingivally) optimized for tooth extrusion movement (e.g., anterior extrusions). FIGS. 9H through 9J illustrate attachments, including horizontal beveled incisally (FIGS. 9H and 9I) and vertical rectangular (FIG. 9J), positioned for intrusion movements (e.g., anterior intrusion with no bicuspid rotation and anterior intrusion plus bicuspid rotation). FIG. 9K illustrates attachments (e.g., vertical rectangular attachments with placement on two teeth adjacent to the extraction site) selected and positioned for lower incisor extraction. FIG. 9L illustrates attachments (e.g., vertical rectangular with placement on two teeth distal and one mesial to the extraction site) selected and positioned for bicuspid extraction.

As described above, a patient's teeth are generally progressively repositioned according to a treatment plan. Exemplary methods for treatment plan design, as well as appliance design and fabrication are described further below. Typically, appliance and/or treatment plan design can optionally, though not necessarily, be accomplished using various computer based applications. It will be recognized that appliance design and fabrication is not limited to any particular method and can include various computer and non-computer based methodologies.

Treatment planning, according to one embodiment of the present invention, is described. Patient data can be collected and analyzed, and specific treatment steps specified and/or prescribed. In one embodiment, a treatment plan can be generated and proposed for a dental practitioner to review. The dental practitioner can accept or request modifications to the treatment plan. Once the treatment plan is approved, manufacturing of appliance(s) can begin. Digital treatment plans are now possible with 3-dimensional orthodontic treatment planning tools such as software at Align Technology, Inc. or other software available from eModels and OrthoCAD, among others. These technologies allow the clinician to use the actual patient's dentition as a starting point for customizing the treatment plan. The software technology of Align Technology, Inc., uses a patient-specific digital model to plot a treatment plan, and then uses a scan of the achieved or actual treatment outcome to assess the degree of success of the outcome as compared to the original digital treatment plan as discussed in U.S. patent application Ser. No. 10/640,439, filed Aug. 21, 2003 and U.S. patent application Ser. No. 10/225,889 filed Aug. 22, 2002.

Figure 10A:
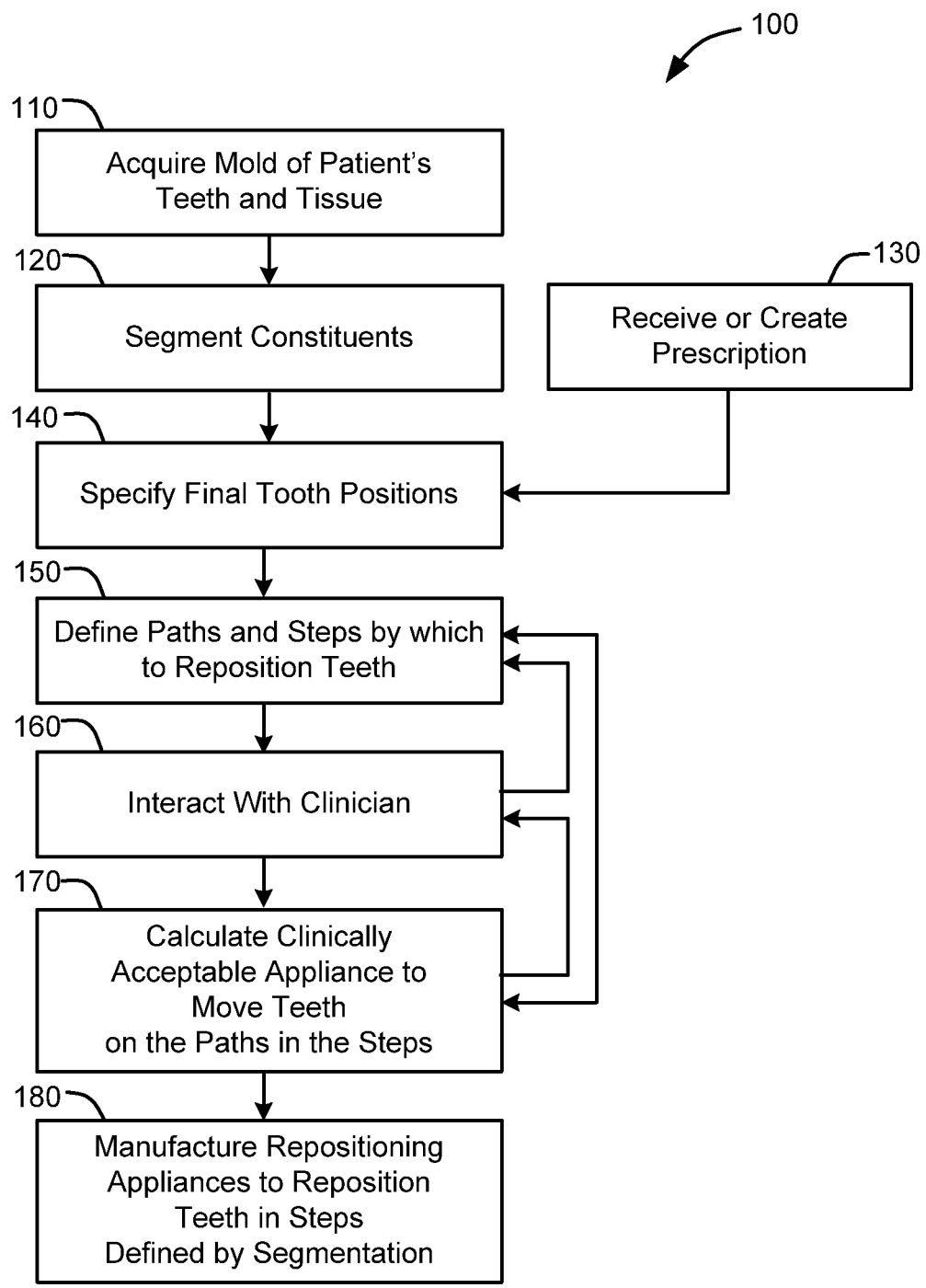
FIG. 10A is a flowchart of a process of specifying a course of treatment according to an embodiment of the present invention.

FIG. 10A illustrates the general flow of an exemplary process 100 for generating a treatment plan or defining and generating repositioning appliances for orthodontic treatment of a patient. The process 100 can incorporate optimized and/or customized attachments and design thereof as further described herein. The process 100 includes the methods, and is suitable for optimized and/or customized attachments and apparatus, of the present invention, as will be described. The computational steps of the process are advantageously implemented as computer program modules for execution on one or more conventional digital computers.

As an initial step, a mold or a scan of patient's teeth or mouth tissue is acquired (step 110). This step generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents the initial (that is, pretreatment) arrangement of the patient's teeth and other tissues.

The initial digital data set, which may include both raw data from scanning operations and data representing surface models derived from the raw data, is processed to segment the tissue constituents from each other (step 120). In particular, in this step, data structures that digitally represent individual tooth crowns are produced. Advantageously, digital models of entire teeth are produced, including measured or extrapolated hidden surfaces and root structures as well as surrounding bone and soft tissue.

The desired final position of the teeth—that is, the desired and intended end result of the orthodontic treatment or phase of orthodontic treatment—can be received from a clinician in the form of a prescription, can be calculated from basic orthodontic principles, or can be extrapolated computationally from a clinical prescription (step 130). With a specification of the desired final positions of the teeth and a digital representation of the teeth themselves, the final position and surface geometry of each tooth can be specified (step 140) to form a complete model of the teeth at the desired end of treatment. Generally, in this step, the position of every tooth is specified. The result of this step may be a set of digital data structures that represents an orthodontically correct repositioning of the modeled teeth relative to presumed-stable tissue for the desired phase of orthodontic treatment. The teeth and tissue are both represented as digital data.

Having both a beginning position and a final position for each tooth, the process next defines a tooth path for the motion of each tooth (step 150). In one embodiment, the tooth paths are optimized in the aggregate so that the teeth are moved in the quickest fashion with the least amount of round-tripping to bring the teeth from their initial positions to their desired final positions. Round-tripping is any motion of a tooth in any direction other than directly toward the desired final position. Round-tripping is sometimes necessary to allow teeth to move past each other. The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation (step 170), which may determine that at one or more points along one or more tooth paths, the forces that can be generated by the appliance on the then-existing configuration of teeth and tissue is incapable of effecting the repositioning that is represented by one or more tooth path segments. With this information, the sub-process defining segmented paths (step 150) can recalculate the paths or the affected sub-paths.

At various stages of the process, and in particular after the segmented paths have been defined, the process can, and generally will, interact with a clinician responsible for the treatment of the patient (step 160). Clinician interaction can be implemented using a client process programmed to receive tooth positions and models, as well as path information from a server computer or process in which other steps of process 100 are implemented. The client process is advantageously programmed to allow the clinician to display an animation of the positions and paths and to allow the clinician to reset the final positions of one or more of the teeth and to specify constraints to be applied to the segmented paths. If the clinician makes any such changes, the sub-process of defining segmented paths (step 150) is performed again.

The segmented tooth paths and associated tooth position data are used to calculate clinically acceptable appliance configurations (or successive changes in appliance configuration) that will move the teeth on the defined treatment path in the steps specified by the path segments (step 170). Each appliance configuration represents a step along the treatment path for the patient. The steps are defined and calculated so that each discrete position can follow straight-line tooth movement or simple rotation from the tooth positions achieved by the preceding discrete step and so that the amount of repositioning required at each step involves an orthodontically optimal amount of force on the patient's dentition. As with the path definition step, this appliance calculation step can include interactions and even iterative interactions with the clinician (step 160). The operation of a process step 200 implementing this step will be described more fully below with reference to FIG. 10B.

Having calculated appliance definitions, the process 100 can proceed to the manufacturing step (step 180) in which appliances defined by the process are manufactured, or electronic or printed information is produced that can be used by a manual or automated process to define appliance configurations or changes to appliance configurations.

Figure 10B:
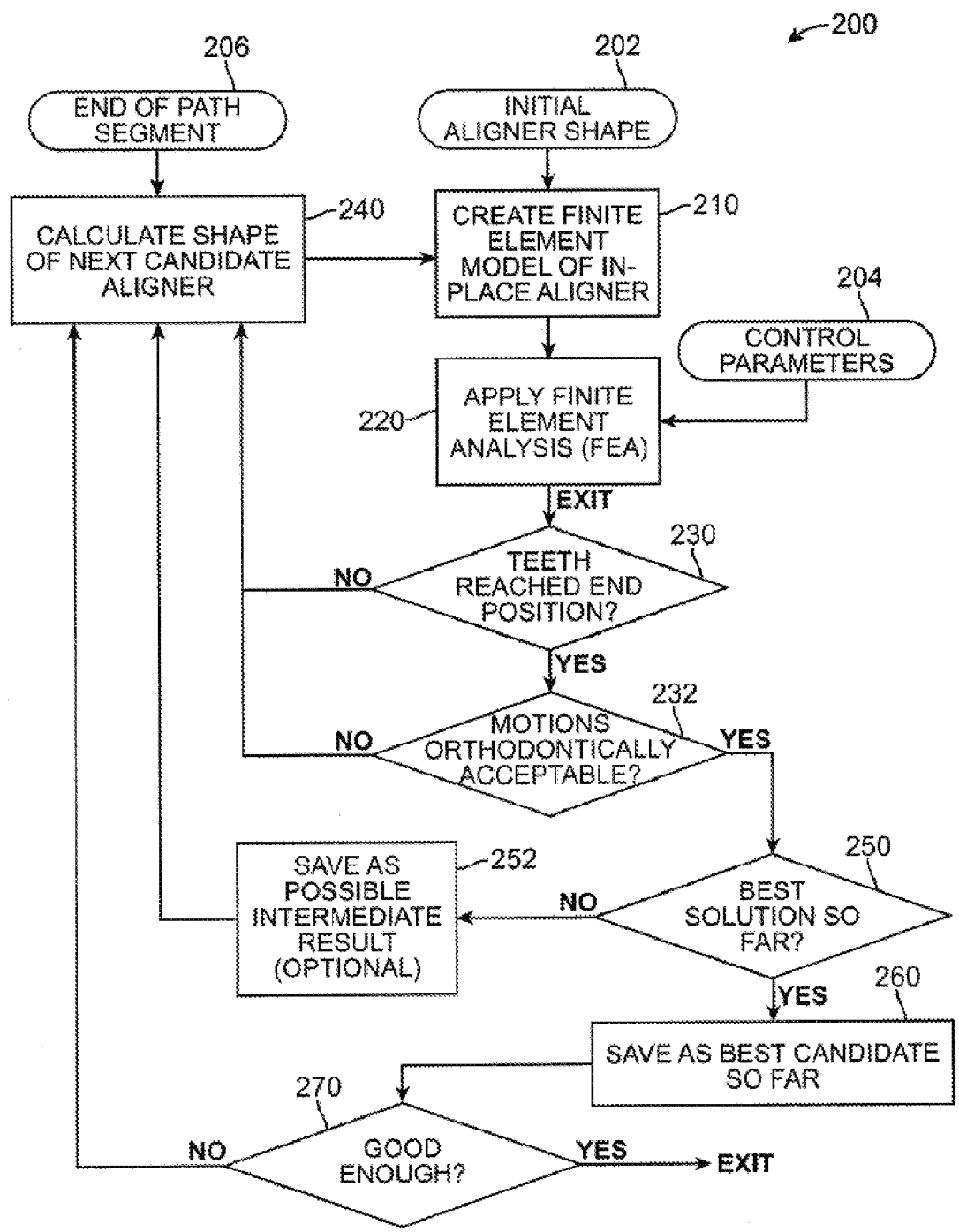
FIG. 10B is a process for calculating aligner shapes.

FIG. 10B illustrates a process 200 implementing the appliance-calculation step (FIG. 6A, step 170) for polymeric shell aligners of the kind described in above-mentioned U.S. Pat. No. 5,975,893. Inputs to the process include an initial aligner shape 202, various control parameters 204, and a desired end configuration for the teeth at the end of the current treatment path segment 206. Other inputs include digital models of the teeth in position in the jaw, models of the jaw tissue, attachment placement and configuration, and specifications of an initial aligner shape and of the aligner material. Using the input data, the process creates a finite element model of the aligner, attachments, teeth and tissue, with the aligner in place on the teeth (step 210). Next, the process applies a finite element analysis to the composite finite element model of aligner, teeth, tissue, etc. (step 220). The analysis runs until an exit condition is reached, at which time the process evaluates whether the teeth have reached the desired end position for the current path segment, or a position sufficiently close to the desired end position (step 230). If an acceptable end position is not reached by the teeth, the process calculates a new candidate aligner shape (step 240). If an acceptable end position is reached, the motions of the teeth calculated by the finite elements analysis are evaluated to determine whether they are orthodontically acceptable (step 232). If they are not, the process also proceeds to calculate a new candidate aligner shape (step 240). If the motions are orthodontically acceptable and the teeth have reached an acceptable position, the current aligner shape is compared to the previously calculated aligner shapes. If the current shape is the best solution so far (step 250), it is saved as the best candidate so far (step 260). If not, it is saved in an optional step as a possible intermediate result (step 252). If the current aligner shape is the best candidate so far, the process determines whether it is good enough to be accepted (step 270). If it is, the process exits. Otherwise, the process continues and calculates another candidate shape (step 240) for analysis.

The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including the PolyFEM product available from CADSI of Coralville, Iowa, the Pro/Mechanica simulation software available from Parametric Technology Corporation of Waltham, Mass., the I-DEAS design software products available from Structural Dynamics Research Corporation (SDRC) of Cincinnati, Ohio, and the MSC/NASTRAN product available from Mac-Neal-Schwendler Corporation of Los Angeles, Calif.

Figure 11:
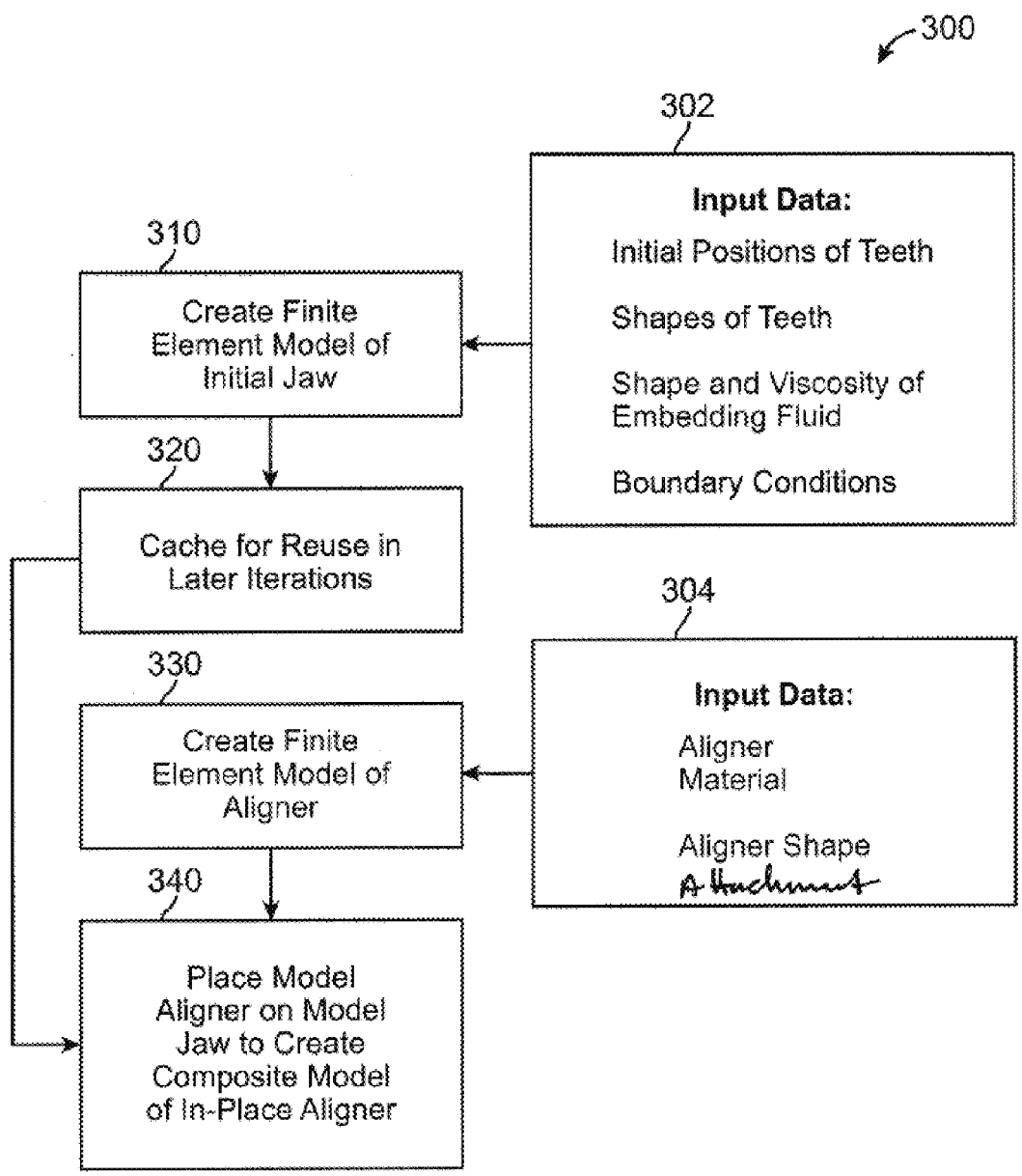
FIG. 11 is a flowchart of a process for creating finite element models.

FIG. 11 shows a process 300 of creating a finite element model that can be used to perform step 210 of the process 200 (FIG. 10B). Input to the model creation process 300 includes input data 302 describing the teeth and tissues and input data 304 describing the aligner. The input data describing the teeth 302 include the digital models of the teeth; digital models of rigid tissue structures, if available; shape and viscosity specifications for a highly viscous fluid modeling the substrate tissue in which the teeth are embedded and to which the teeth are connected, in the absence of specific models of those tissues; and boundary conditions specifying the immovable boundaries of the model elements. In one implementation, the model elements include only models of the teeth, a model of a highly viscous embedding substrate fluid, and boundary conditions that define, in effect, a rigid container in which the modeled fluid is held. Note that fluid characteristics may differ by patient clusters, for example as a function of age.

A finite element model of the initial configuration of the teeth and tissue is created (step 310) and optionally cached for reuse in later iterations of the process (step 320). As was done with the teeth and tissue, a finite element model is created of the polymeric shell aligner (step 330). The input data for this model includes data specifying the material of which the aligner is made and the shape of the aligner (data input 304), and may optionally further include attachment information.

The model aligner is then computationally manipulated to place it over the modeled teeth in the model jaw to create a composite model of an in-place aligner (step 340). Optionally, the forces required to deform the aligner to fit over the teeth, including any hardware attached to the teeth, are computed and used as a figure of merit in measuring the acceptability of the particular aligner configuration. Optionally, the tooth positions used are as estimated from a probabilistic model based on prior treatment steps and other patient information. In a simpler alternative, however, the aligner deformation is modeled by applying enough force to its insides to make it large enough to fit over the teeth, placing the model aligner over the model teeth in the composite model, setting the conditions of the model teeth and tissue to be infinitely rigid, and allowing the model aligner to relax into position over the fixed teeth. The surfaces of the aligner and the teeth are modeled to interact without friction at this stage, so that the aligner model achieves the correct initial configuration over the model teeth before finite element analysis is begun to find a solution to the composite model and compute the movement of the teeth under the influence of the distorted aligner.

Figure 12:
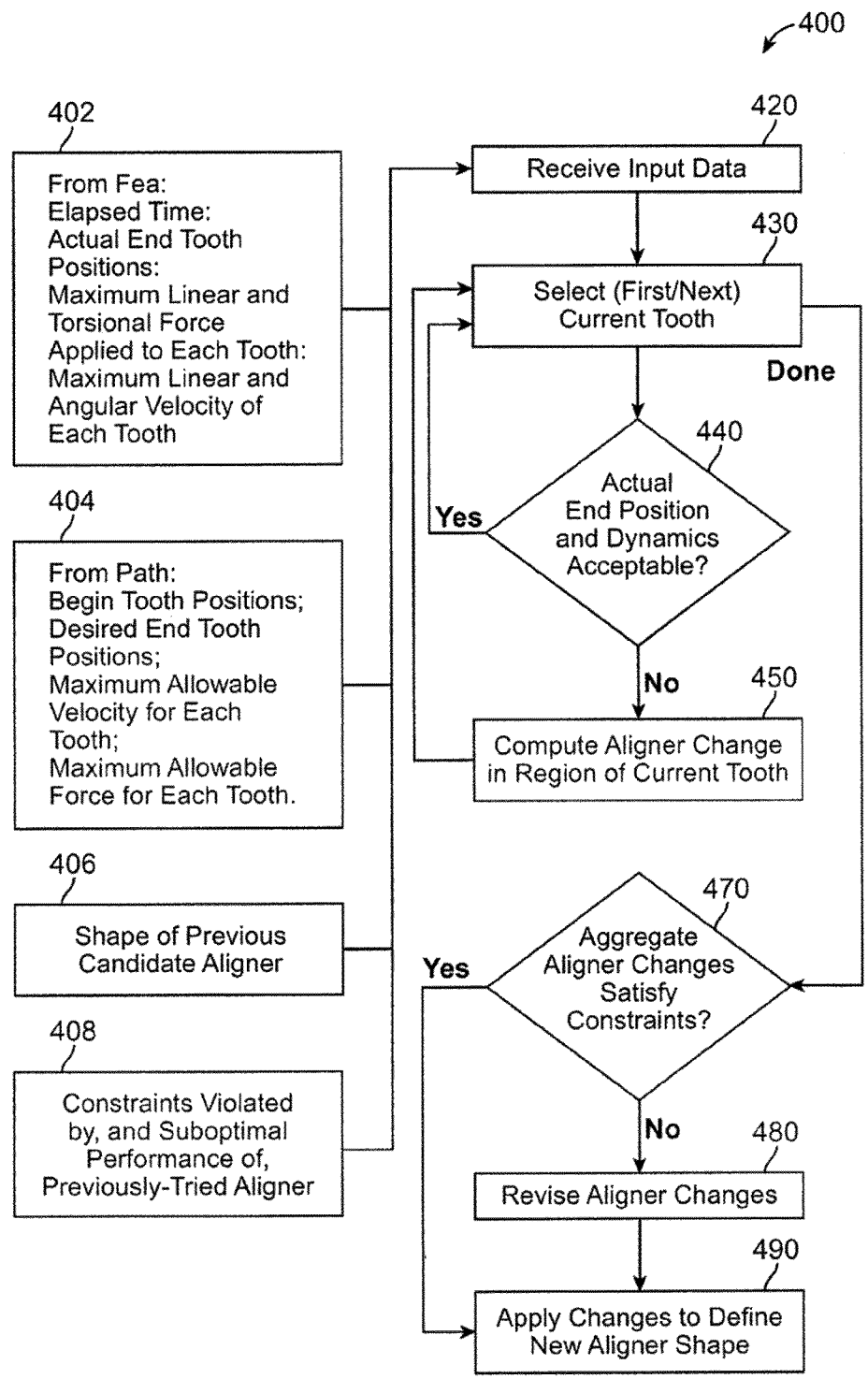
FIG. 12 is a flowchart of a process for calculating changes in aligner shape.

FIG. 12 shows a process 400 for calculating the shape of a next aligner that can be used in the aligner calculations, as described in step 240 of process 200 (FIG. 10B). A variety of inputs are used to calculate the next candidate aligner shape. These include inputs 402 of data generated by the finite element analysis solution of the composite model and data 404 defined by the current tooth path. The data 402 derived from the finite element analysis includes the amount of real elapsed time over which the simulated repositioning of the teeth took place; the actual end tooth positions calculated by the analysis; the maximum linear and torsional force applied to each tooth; and the maximum linear and angular velocity of each tooth. From the input path information, the input data 404 includes the initial tooth positions for the current path segment, the desired tooth positions at the end of the current path segment, the maximum allowable displacement velocity for each tooth, and the maximum allowable force of each kind for each tooth.

If a previously evaluated aligner was found to violate one or more constraints, additional input data 406 can optionally be used by the process 400. This data 406 can include information identifying the constraints violated by, and any identified suboptimal performance of, the previously evaluated aligner. Additionally, input data 408 relating to constraints violated by, and suboptimal performance of previous dental devices can be used by the process 400.

Having received the initial input data (step 420), the process iterates over the movable teeth in the model. (Some of the teeth may be identified as, and constrained to be, immobile.) If the end position and dynamics of motion of the currently selected tooth by the previously selected aligner is acceptable ("yes" branch of step 440), the process continues by selecting for consideration a next tooth (step 430) until all teeth have been considered ("done" branch from step 430 to step 470). Otherwise ("no" branch from step 440), a change in the aligner is calculated in the region of the currently selected tooth (step 450). The process then moves back to select the next current tooth (step 430) as has been described.

When all of the teeth have been considered, the aggregate changes made to the aligner are evaluated against previously defined constraints (step 470), examples of which have already been mentioned. Constraints can be defined with reference to a variety of further considerations, such as manufacturability. For example, constraints can be defined to set a maximum or minimum thickness of the aligner material, or to set a maximum or minimum coverage of the aligner over the crowns of the teeth. If the aligner constraints are satisfied, the changes are applied to define a new aligner shape (step 490). Otherwise, the changes to the aligner are revised to satisfy the constraints (step 480), and the revised changes are applied to define the new aligner shape (step 490).

Figure 13A:
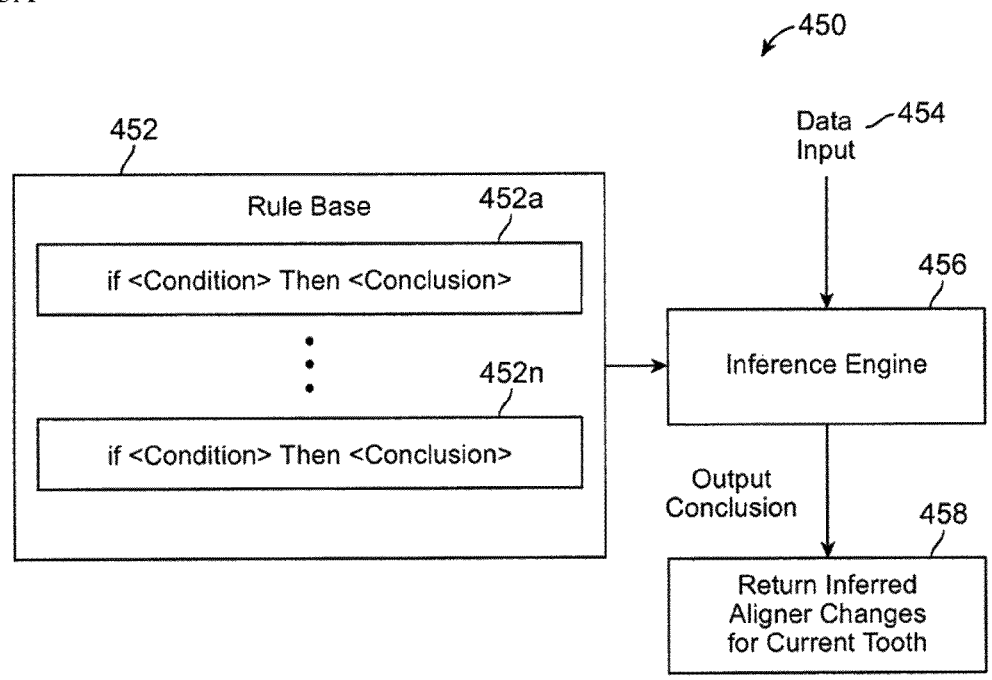
FIG. 13A is a flowchart of a subprocess for calculating changes in aligner shape.

FIG. 13A illustrates one implementation of the step of computing an aligner change in a region of a current tooth (step 450 in FIG. 12). In this implementation, a rule-based inference engine 456 is used to process the input data previously described (input 454) and a set of rules 452a-452n in a rule base of rules 452. The inference engine 456 and the rules 452 define a production system which, when applied to the factual input data, produces a set of output conclusions that specify the changes to be made to the aligner in the region of the current tooth (output 458).

Rules 452a . . . 452n have the conventional two-part form: an if-part defining a condition and a then-part defining a conclusion or action that is asserted if the condition is satisfied. Conditions can be simple or they can be complex conjunctions or disjunctions of multiple assertions. An exemplary set of rules, which defines changes to be made to the aligner, includes the following: if the motion of the tooth is too fast, add driving material to the aligner opposite the desired direction of motion; if the motion of the tooth is too slow, add driving material to overcorrect the position of the tooth; if the tooth is too far short of the desired end position, add material to overcorrect; if the tooth has been moved too far past the desired end position, add material to stiffen the aligner where the tooth moves to meet it; if a maximum amount of driving material has been added, add material to overcorrect the repositioning of the tooth and do not add driving material; and if the motion of the tooth is in a direction other than the desired direction, remove and add material so as to redirect the tooth.

Figure 13B:
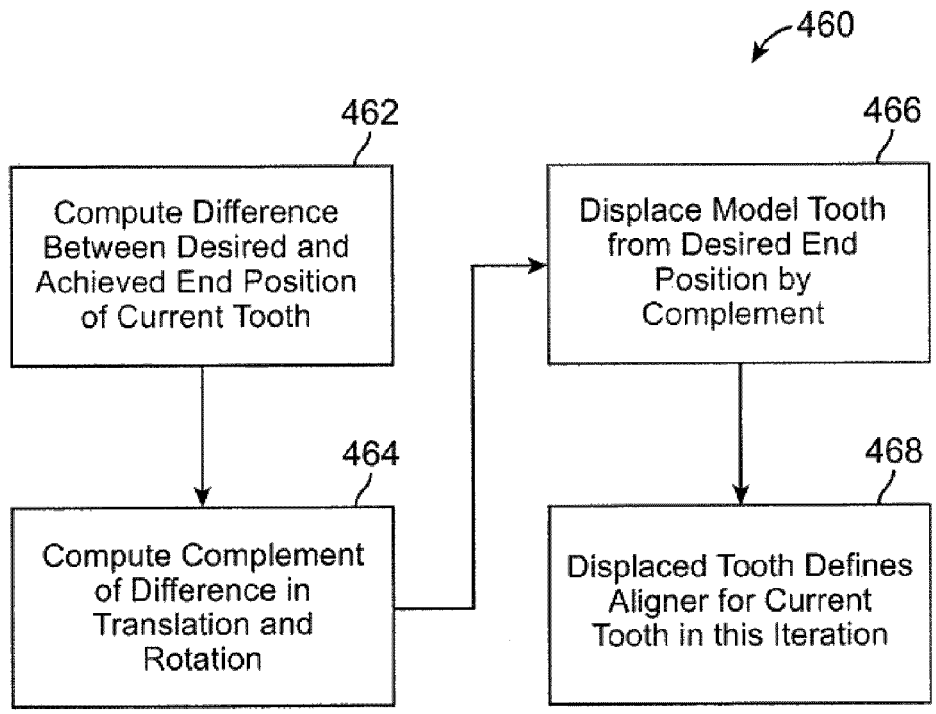
FIG. 13B is a flowchart of a subprocess for calculating changes in aligner shape.
Figure 13C:
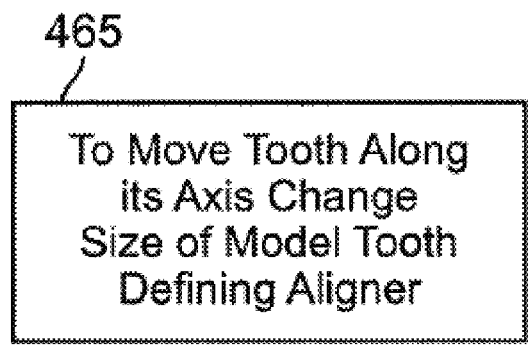
FIG. 13C is a flowchart of a subprocess for calculating changes in aligner shape.

In an alternative embodiment, illustrated in FIGS. 13B and 13C, an absolute configuration of the aligner is computed, rather than an incremental difference. As shown in FIG. 13B, a process 460 computes an absolute configuration for an aligner in a region of a current tooth. Using input data that has already been described, the process computes the difference between the desired end position and the achieved end position of the current tooth (step 462). Using the intersection of the tooth center line with the level of the gum tissue as the point of reference, the process computes the complement of the difference in all six degrees of freedom of motion, namely three degrees of translation and three degrees of rotation (step 464). Next, the model tooth is displaced from its desired end position by the amounts of the complement differences (step 466), which is illustrated in FIG. 13B.

Figure 13D:
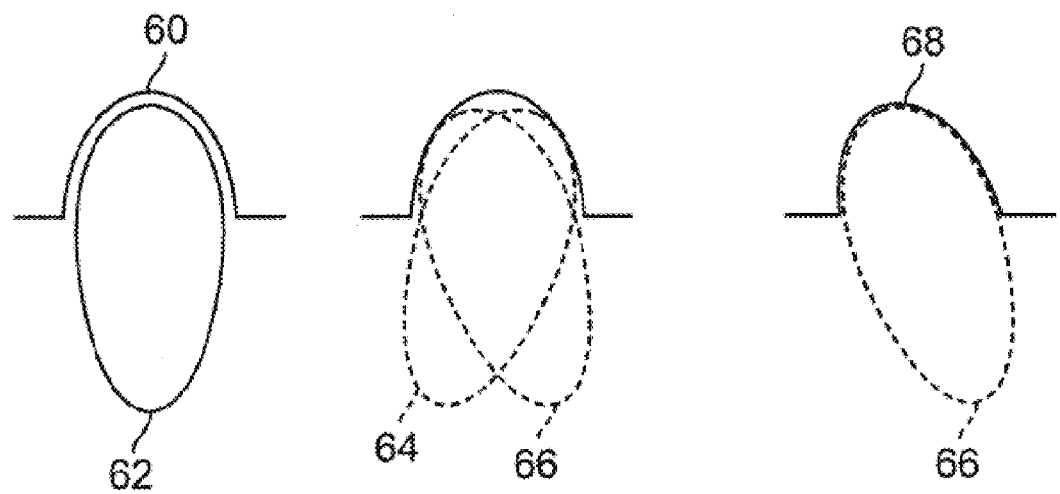
FIG. 13D is a schematic illustrating the operation of the subprocess of FIG. 13B.

FIG. 13D shows a planar view of an illustrative model aligner 60 over an illustrative model tooth 62. The tooth is in its desired end position and the aligner shape is defined by the tooth in this end position. The actual motion of the tooth calculated by the finite element analysis is illustrated as placing the tooth in position 64 rather than in the desired position 62. A complement of the computed end position is illustrated as position 66. The next step of process 460 (FIG. 13B) defines the aligner in the region of the current tooth in this iteration of the process by the position of the displaced model tooth (step 468) calculated in the preceding step (step 466). This computed aligner configuration in the region of the current tooth is illustrated in FIG. 13D as shape 68 which is defined by the repositioned model tooth in position 66.

A further step in process 460, which can also be implemented as a rule 452 (FIG. 13A), is shown in FIG. 13C. To move the current tooth in the direction of its central axis, the size of the model tooth defining that region of the aligner, or the amount of room allowed in the aligner for the tooth, is made smaller in the area away from which the process has decided to move the tooth (step 465).

Figure 14:
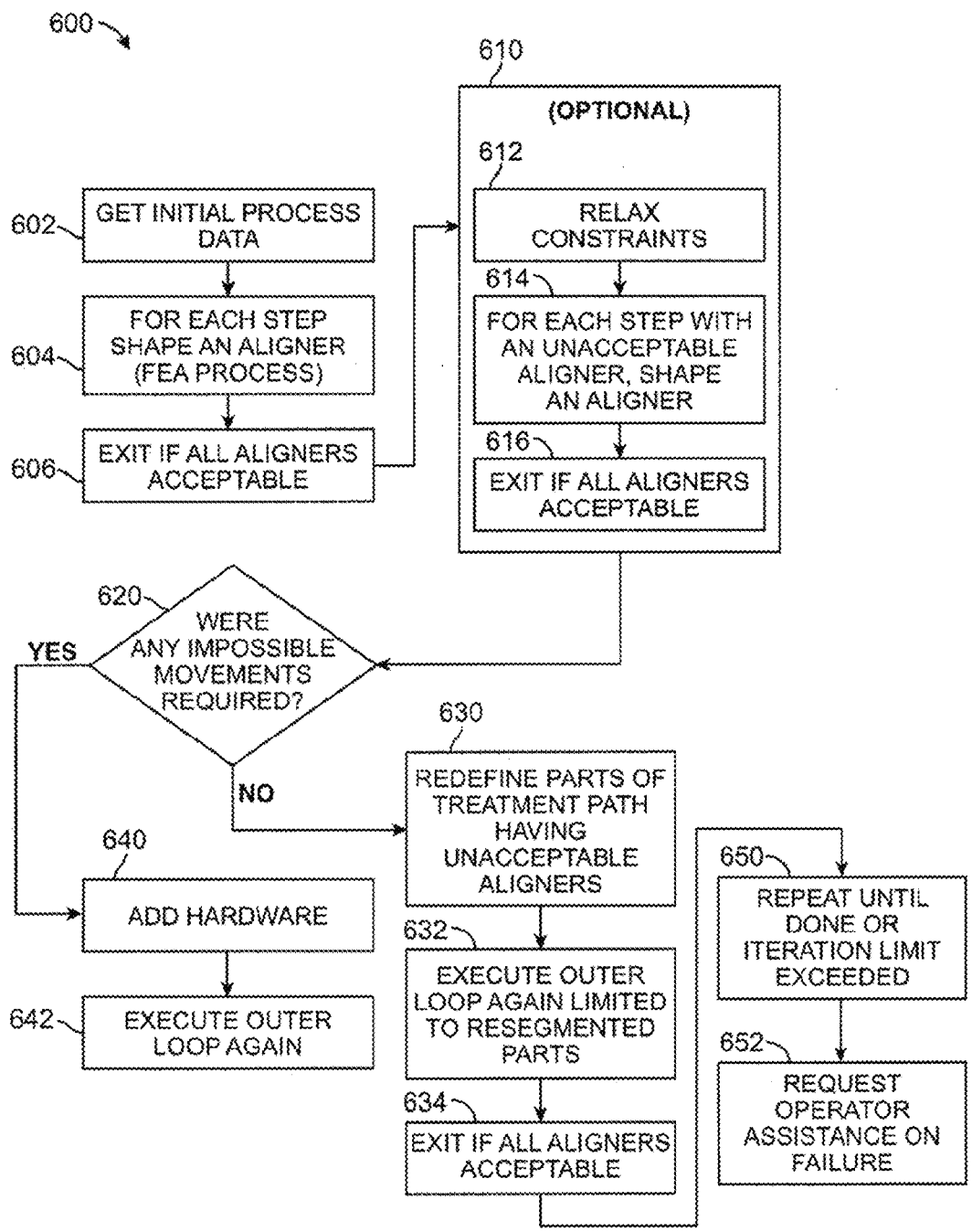
FIG. 14 is a flowchart of a process for computing shapes for sets of aligners.

As shown in FIG. 14, the process 200 (FIG. 10B) of computing the shape for an aligner for a step in a treatment path is one step in a process 600 of computing the shapes of a series of aligners. This process 600 begins with an initialization step 602 in which initial data, control and constraint values are obtained.

When an aligner configuration has been found for each step or segment of the treatment path (step 604), the process 600 determines whether all of the aligners are acceptable (step 606). If they are, the process is complete. Otherwise, the process optionally undertakes a set of steps 610 in an attempt to calculate a set of acceptable aligners. First, one or more of the constraints on the aligners is relaxed (step 612). Then, for each path segment with an unacceptable aligner, the process 200 (FIG. 10B) of shaping an aligner is performed with the new constraints (step 614). If all the aligners are now acceptable, the process 600 exits (step 616).

Aligners may be unacceptable for a variety of reasons, some of which are handled by the process. For example, if any impossible movements were required (step 620), that is, if the shape calculation process 200 (FIG. 10B) was required to effect a motion for which no rule or adjustment was available, the process 600 proceeds to execute a module that calculates the configuration of a hardware attachment to the subject tooth to which forces can be applied to effect the required motion (step 640). Because adding hardware can have an effect that is more than local, when hardware is added to the model, the outer loop of the process 600 is executed again (step 642).

If no impossible movements were required ("no" branch from step 620), the process transfers control to a path definition process (such as step 150, FIG. 10A) to redefine those parts of the treatment path having unacceptable aligners (step 630). This step can include both changing the increments of tooth motion, i.e., changing the segmentation, on the treatment path, changing the path followed by one or more teeth in the treatment path, or both. After the treatment path has been redefined, the outer loop of the process is executed again (step 632). The recalculation is advantageously limited to recalculating only those aligners on the redefined portions of the treatment path. If all the aligners are now acceptable, the process exits (step 634). If unacceptable aligners still remain, the process can be repeated until an acceptable set of aligners is found or an iteration limit is exceeded (step 650). At this point, as well as at other points in the processes that are described in this specification, such as at the computation of additional hardware (step 640), the process can interact with a human operator, such as a clinician or technician, to request assistance (step 652). Assistance that an operator provides can include defining or selecting suitable attachments to be attached to a tooth or a bone, defining an added elastic element to provide a needed force for one or more segments of the treatment path, suggesting an alteration to the treatment path, either in the motion path of a tooth or in the segmentation of the treatment path, and approving a deviation from or relaxation of an operative constraint.

As was mentioned above, the process 600 is defined and parameterized by various items of input data (step 602). In one implementation, this initializing and defining data includes the following items: an iteration limit for the outer loop of the overall process; specification of figures of merit that are calculated to determine whether an aligner is good enough (see FIG. 10B, step 270); a specification of the aligner material; a specification of the constraints that the shape or configuration of an aligner must satisfy to be acceptable; a specification of the forces and positioning motions and velocities that are orthodontically acceptable; an initial treatment path, which includes the motion path for each tooth and a segmentation of the treatment path into segments, each segment to be accomplished by one aligner; a specification of the shapes and positions of any anchors installed on the teeth or otherwise; and a specification of a model for the jaw bone and other tissues in or on which the teeth are situated (in the implementation being described, this model consists of a model of a viscous substrate fluid in which the teeth are embedded and which has boundary conditions that essentially define a container for the fluid).

Various tooth root imaging and/or modeling (e.g., statistical root modeling) may be utilized. The teeth movement can be guided in part using a root-based sequencing system. In one embodiment, the movement is constrained by a surface area constraint, while in another embodiment, the movement is constrained by a volume constraint.

Optionally, other features are added to the tooth model data sets to produce desired features in the aligners. For example, it may be desirable to add digital wax patches to define cavities or recesses to maintain a space between the aligner and particular regions of the teeth or jaw. It may also be desirable to add digital wax patches to define corrugated or other structural forms to create regions having particular stiffness or other structural properties. In manufacturing processes that rely on generation of positive models to produce the repositioning appliance, adding a wax patch to the digital model will generate a positive mold that has the same added wax patch geometry. This can be done globally in defining the base shape of the aligners or in the calculation of particular aligner shapes. One feature that can be added is a rim around the gumline, which can be produced by adding a digital model wire at the gumline of the digital model teeth from which the aligner is manufactured. When an aligner is manufactured by pressure fitting polymeric material over a positive physical model of the digital teeth, the wire along the gumlines causes the aligner to have a rim around it providing additional stiffness along the gumline.

In another optional manufacturing technique, two or more sheets of material are pressure fit over the positive tooth model, where one of the sheets is cut along the apex arch of the aligner and the other(s) is overlaid on top. This provides at least a double thickness of aligner material along the vertical walls of the teeth.

The changes that can be made to the design of an aligner are constrained by the manufacturing technique that will be used to produce it. For example, if the aligner will be made by pressure fitting a polymeric sheet over a positive model, the thickness of the aligner is determined by the thickness of the sheet. As a consequence, the system will generally adjust the performance of the aligner by changing the orientation of the model teeth, the sizes of parts of the model teeth, the position and selection of attachments, and the addition or removal of material (e.g., adding virtual wires, adding/removing attachment material, modifying one or more attachment parameters, and creating modification (e.g., modifications to compensate for protrusion mediated distortions)) to change the structure of the aligner. The system can optionally adjust the aligner by specifying that one or more of the aligners are to be made of a sheet of a thickness other than the standard one, to provide more or less force to the teeth. On the other hand, if the aligner will be made by a stereo lithography process, the thickness of the aligner can be varied locally, and structural features such as attachment recesses or engagement portions, rims, dimples, and corrugations can be added without modifying the digital model of the teeth. The system can also be used to model the effects of more traditional appliances such as retainers and braces and therefore be used to generate optimal designs and treatment programs for particular patients.

Thus, one or more tooth attachments can be selectively added, modified/customized, and included in appliance design and fabrication, with appliance and attachment design and fabrication, and incorporation of appliances in a treatment plan as described above. In some instances, however, incorporation of an attachment into an appliance design may result in a subsequent change in the geometry of the appliance at other surfaces of the appliance, e.g., when worn by the patient. Such changes or alterations can result in changes in property or location of contact surfaces between the tooth and the appliance, sometimes in a manner that more optimally imparts a desired force system to the patient's tooth as well as sometimes in an undesirable manner. As such, changes or distortions can be modeled or accounted for in both attachment and/or appliance design. For example, changes, distortions and the like can be analyzed or determined computationally in terms of probability of occurrence, as well as whether such changes/distortions would be beneficial or detrimental to the desired loading and tooth movement. Methods can be included to determine the effect of these geometric changes and compensate for them by identifying new surfaces or shapes, and loadings to accomplish the desired movement. Appliance geometry and attachment parameters can therefore be improved in this iterative design process, as the process in turn considers each feature and its effect on the appliance geometry, on surfaces of contact, and on the force system produced in the designing of an orthodontic system.

Figure 15A:
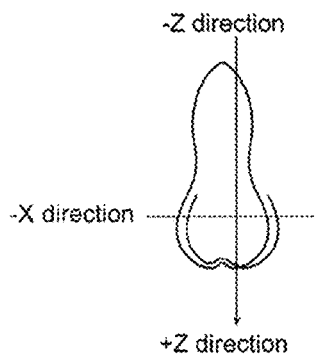
FIGS. 15A-15B illustrate an initial tooth position with a positioned dental appliance, and a resulting undesirable force vector, respectively.
Figure 15B:
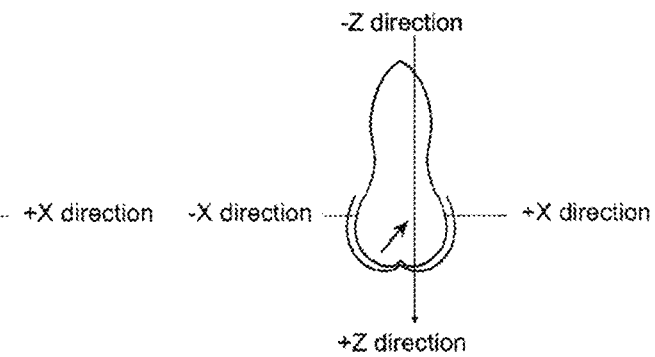

Modification of an appliance surface to compensate for an effect (e.g., distortion effect) due to incorporation of an attachment in a treatment plan, according to an embodiment of the present invention, is illustrated with reference to FIGS. 15A-15D, and FIG. 16. FIGS. 15A-15B illustrate an initial tooth position with a positioned dental appliance, and a resulting undesirable force vector, respectively. Referring to the Figures, in an example where the tooth as shown is being moved in a facial direction along the x-direction, upon positioning of the dental appliance such as the polymeric shell aligner, over the tooth, the aligner shape geometry is configured to apply a predetermined force upon the tooth to reposition the tooth in accordance with a treatment plan for the particular treatment stage. For example, as shown in FIG. 15B, the dental appliance is configured to fit over the tooth to reposition the tooth in the x-direction as shown, but, rather, results in the application of a predetermined force in the +x/−z direction as shown and illustrated by the arrow. Appliances can include one or more shaped features disposed in a cavity.

Figure 15C:
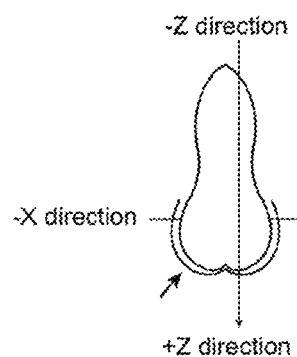
Figure 15C:
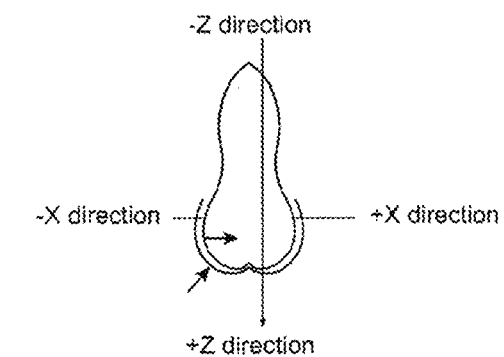

Accordingly, in one aspect, the aligner shape geometry and/or attachment parameters may be optimized to compensate for the undesirable but resulting force vector so as to counteract its force and further, to apply the intended force in the direction based on the treatment plan for the treatment stage under consideration. One exemplary modification to an aligner can include addition of a relief component. FIGS. 15C-15D illustrate a relief addition to the dental appliance to counteract the undesirable force vector around the tooth, and the resulting desired application of the predetermined force on the tooth by the dental appliance, respectively. In one aspect, to compensate for the undesirable force (for example, as shown in FIG. 15B by the arrow), a predetermined relief (for example, but not limited to, 0.1 to 0.3 mm) may be provided such that the contact between the aligner and the tooth that resulted in the undesirable force vector is avoided, but still retaining the desired force, for example, along the x-axis as discussed above.

Referring to FIG. 15C, the predetermined relief on the aligner is illustrated by the arrow, whereby the engagement between the aligner and the tooth at the location resulting in the undesirable force is removed by modifying the shape of the aligner geometry. In this manner, in one aspect, and as shown in FIG. 15D, the intended and desirable force applied upon the tooth for example, in the x-direction, is achieved by, for example, modifying the aligner shape geometry.

Figure 16:
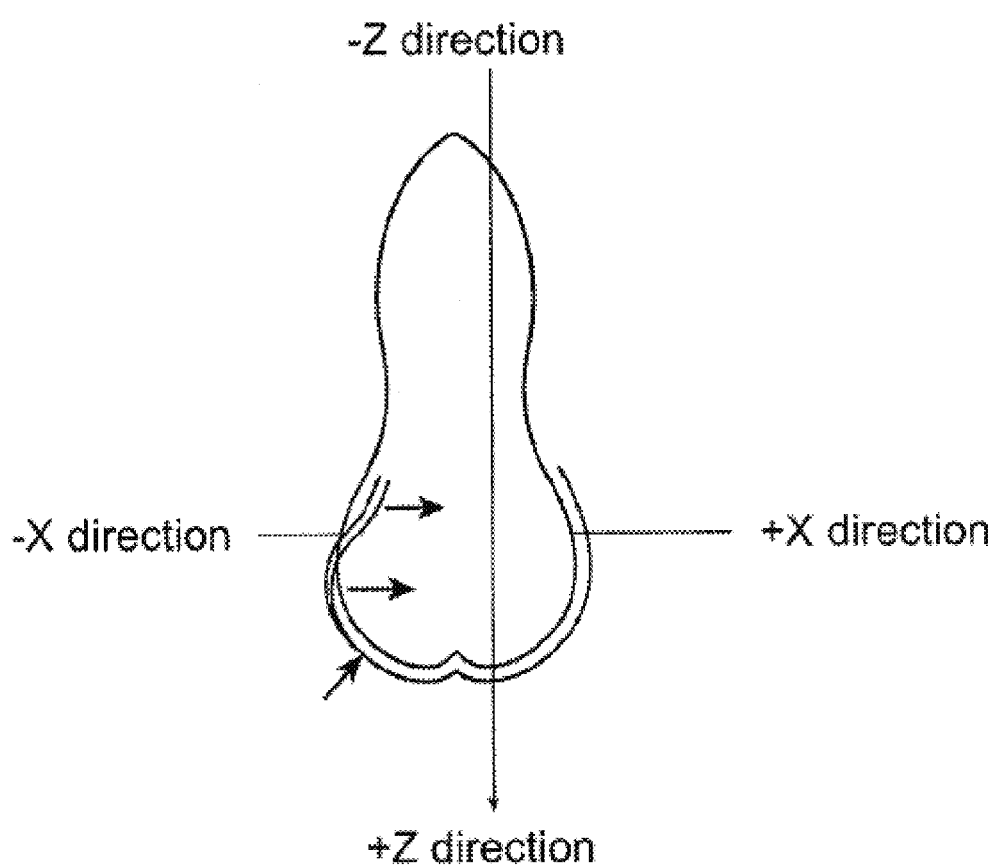
FIG. 16 illustrates a modified dental appliance geometry including an additional shape modification to remove a gap between the dental appliance and the tooth.

FIG. 16 illustrates a modified dental appliance geometry including an additional shape modification to remove a gap between the dental appliance and the tooth. Referring to FIG. 16, it is to be noted that while the modification of the aligner shape geometry (for example, discussed above in conjunction with FIGS. 15C-15D), results in the desired predetermined force applied upon the tooth as planned for the dental treatment, there may be a gap or pocket that forms between the tooth and the aligner, for example, as shown in FIG. 16, near the gingival area. In one aspect, to account for this gap or pocket generated, the aligner shape geometry may be further modified or optimized, for example, to better adapt in the direction towards the tooth when the aligner is in the active (or stretched) state.

Referring to FIG. 16, the optimization of the aligner shape geometry to address the formed gap or pocket is illustrated by the arrow in one embodiment, in the direction of which the aligner shape may be modified. Moreover, it should be noted that the optimization of the aligner shape to account for the gap may potentially effect the direction of the applied force on the tooth by the aligner, and thus, may further require additional modification or optimization.

In one aspect, the modification of an attachment parameter(s) and/or dental aligner shape geometry, e.g., with one or more areas of modification (e.g., relief, etc.), as well as recontouring for looser or tighter adaptation, to achieve the desired force vector, while avoiding friction and other undesirable force vectors provides improved and customized aligner shape for the treatment of the dental conditions. In manufacturing of the dental appliances, in one aspect, the mold may be adjusted during the build process to take shape of the desired geometry based on, for example, digitally adding and/or subtracting the relief and/or attachment contact/engagement portion in predefined or relevant locations of the mold.

In one aspect, based on the force behavior determined from the material properties and the amount of surface area perpendicular to the composite vector resulting from the movement vector for the particular treatment stage, additional surface area may be added to the tooth by employing an attachment that can be selected and further customized for the desired movement. In this manner, in one aspect, the cross section and/or orientation of the surface area may be determined for a particular tooth, and the attachment(s) can be incorporated on one or more teeth to enhance or improve upon the necessary surface area to cooperate or engage with the dental appliance to effect the desired movement vector or the predetermined level of force upon the tooth in the accurate direction for the treatment stage.

In this manner, and as further set forth herein, a dental aligner and/or attachment may be designed, manufactured, or simulated using a computer aided design tool or system, where, a representation of the tooth to be moved is first modeled. Thereafter, the aligner that defines the target position of the tooth is modeled with shape geometry properties defined. Thereafter, the force necessary to reposition the tooth from the initial location to the target location is determined or modeled, for example, using FEA modeling, or other suitable computation and/or modeling techniques. In one aspect, it is possible to define the force using a physical model of the teeth connected to force measurement sensors, such that the optimal forces may be determined using the readouts obtained from the physical model, and thus altering the one or more attachment parameters and aligner configurations based at least in part on the feedback from the physical force gauge.

As a result, a movement vector is defined which establishes the direction of the applied force, as well as the level of force and its properties which are necessary to reposition the tooth from the initial position to the target position. Based on the movement vector, and the modeled aligner and/or attachment, the aligner and/or attachment is further modified or reconfigured to factor in the determined movement vector. That is, after having defined the movement vector which identifies the force properties necessary for the tooth repositioning, the dental appliance shape and/or attachment parameter(s) is altered or optimized based on the determined movement vector. Additionally, the appliance shape and/or attachment parameter(s) may be further optimized to counteract the undesirable forces or force components, or appliance distortion (e.g., due to an attachment) that may result based on the defined movement vector.

Thereafter, the modified or optimized dental appliance may be manufactured through rapid prototyping (e.g., sterolithography) or other suitable techniques to attain the desired tooth movement. Further, this process may be repeated for the optimization of dental appliance for each treatment stage of the treatment plan such that the aligner performance and therefore, the treatment plan result is improved.

Furthermore, in yet still another aspect, attachment design and/or placement may be determined based on the location of the maximum amount of surface area available perpendicular to the desired direction of the tooth movement. Further, if the force on any given tooth in the treatment plan is at or below a predefined level, the attachment(s) may be added to the tooth or appliance to supplement the desired surface area or increase the friction coefficient of the tooth, thereby improving the force profile of the aligner on the tooth.

In one aspect, the data set associated with the teeth, gingiva and/or other oral tissue, or structures may be intentionally altered through, for example, addition, partial or total subtraction, uniform or non-uniform scaling, Boolean or non-Boolean algorithm, or geometric operations, or one or more combinations thereof, for the configuration, modeling and/or manufacturing of the dental appliance that may be optimized for the desired or intended treatment goal.

Moreover, in further regard to the discussion herein regarding attachment design and customization, angulation or the attachment as well as the surface configuration of the attachments may be selected or provided to improve upon the movement vector to optimize its application to the desired tooth while minimizing the amount of undesirable or unwanted force vectors, e.g., that may be counteracting upon the movement vector. Additionally, in one aspect, a plurality of attachments, e.g., a series of abutting attachments may be provided to alter the force direction or generate the movement vector which is carried over for a predetermined time period, such that, the series of abutting attachments may be configured to function as slow motion cams where the dental appliance then functions as a follower.

In still another aspect, point tracing may be added to treat and/or track tooth points over the treatment stages, such that the desired or proper cam/follower relationship may be determined to attain the target position or the treatment goal. In one aspect, one or more protrusions on the interior surface(s) of the dental appliance may be configured as the follower, and which may be formed from virtual pressure points. The virtual pressure points are comprised in one embodiment of voids intentionally built or designed into the reference mold or model, which is associated with corresponding portions in the aligner that are indented to exert additional pressure on the teeth when the aligner is formed over the reference mold.

Accordingly, in one aspect, the n+1 or subsequent/target tooth position is first determined. Thereafter, the direction of movement to reach the target tooth position from the initial tooth position is determined. After determining the direction of movement, the amount or magnitude and direction of force and torque to reposition the tooth from the initial position to the target position is determined. Thereafter, profile of the attachment that would provide the most suitable engagement, grip, and/or load vector in the direction of the planned tooth movement is determined, including, e.g., geometry, position of the attachment relative to the tooth surface, etc.

Having determined the relevant profile/parameters of the attachment(s), the attachment displacement to attain the position translation from the initial position to the target position can be determined. Upon positioning the attachment on the tooth, the dental appliance at the subsequent treatment stage engages with the tooth contacts of the dental appliance via the positioned attachment. In this manner, the force/torque generated by the dental appliance when worn by the patient is accurately directed in the desired direction, and also is configured with sufficient magnitude to move the tooth as intended, such as into the next planned position. For example, in one embodiment, the attachments are bonded to the patient's tooth. The initial position of the attachment is determined as described above. The displaced or repositioned attachments may leave a new position of the cavities conforming to the shape of the attachment on the dental appliance. With the attachments on the tooth crown at the initial stage and displaced at the subsequent target treatment stage, the dental appliance of the target treatment stage may interfere with the attachment on the tooth at the initial treatment stage. The interference, in turn, is configured to generate the force/torque to create the desired tooth movement.

In one aspect, the direction and the magnitude of the force/torque may be modified or optimized to generate counterbalancing force/torque to eliminate or minimize unwanted tipping torque, to attain root movement, and the like, by adjusting the profile, parameters, and/or positioning of the attachments relative to the crown surface, for example. The amount of the attachment movement with respect to the tooth crown may also be correlated with the tooth movement to generate a treatment plan based on the movement of the features on the tooth.

Figure 17:
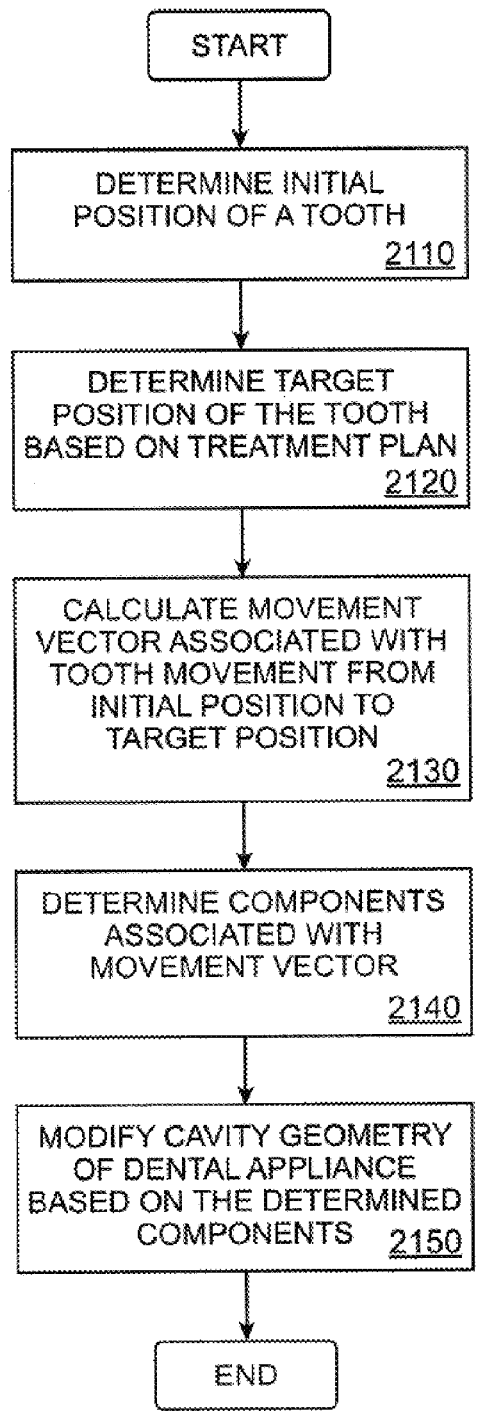
FIG. 17 is a flowchart illustrating the optimized shape geometry of the dental appliance.

FIG. 17 is a flowchart illustrating the optimized shape geometry of the dental appliance, which can be optimized to deliver the desired load to the tooth in combination with one or more attachments positioned on the teeth. Referring to FIG. 17, the initial position of the tooth is determined (step 2110). Thereafter, the target position of the tooth based on the treatment plan is determined (step 2120). In one aspect, the target position may include the next or n+1 treatment stage tooth position. After determining the target position of the tooth based on the treatment plan, a movement vector associated with the tooth movement from the initial position to the target position is calculated or determined (step 2130). That is, a force profile or attributes are determined. The force profile or attributes may include the magnitude of the force and the direction of the force, for example, that is associated with the tooth movement from the initial position to the target position.

After determining the movement vector associated with the tooth movement from the initial position to the target position, the components associated with the movement vector are determined (step 2140). For example, as discussed above, the force magnitude associated with the movement vector to reposition the tooth from the initial position to the target position is determined. Additionally, the force direction for the tooth movement, as well as counter forces for addressing unwanted or unintended forces are determined. Thereafter, based on the determined components associated with the movement vector which is associated with the tooth movement from the initial position to the target position, the cavity geometry of the dental appliance such as the aligner is modified (step 2150).

Figure 18:
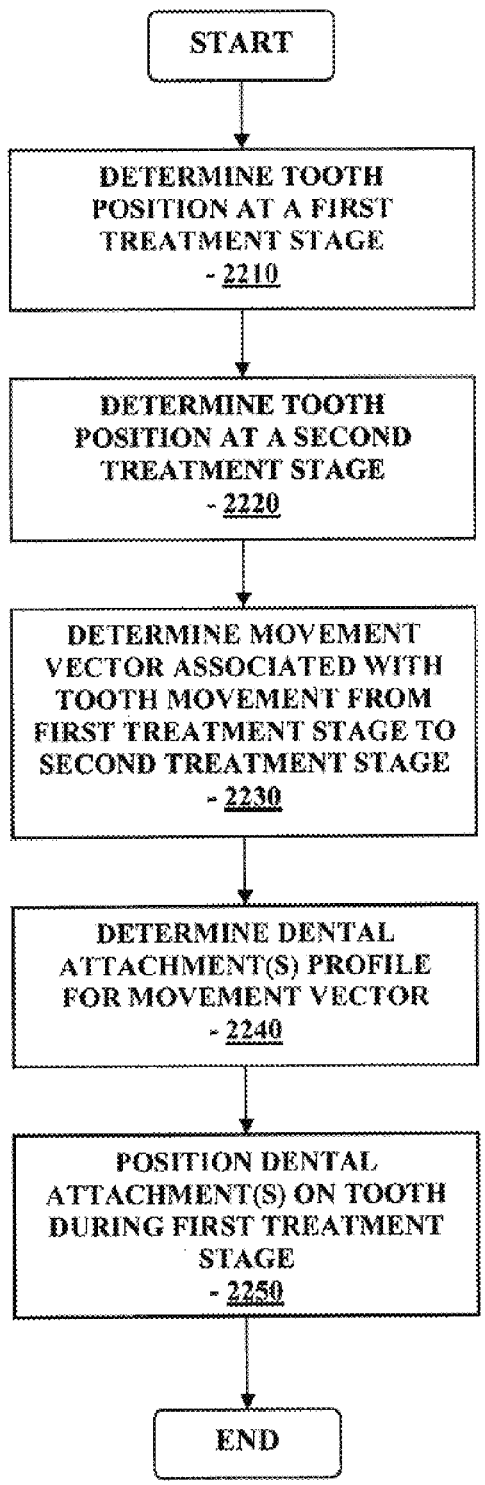
FIG. 18 is a flowchart illustrating the dental attachment positioning.

FIG. 18 is a flowchart illustrating attachment parameter determination, including attachment profile and positioning. Referring to FIG. 18, the tooth position at a first treatment stage is determined (step 2210). The tooth position at the second or n+1 treatment stage is determined (step 2220). Thereafter, the movement vector associated with the tooth movement from the first treatment stage to the second treatment stage is determined (step 2230). After determining the movement vector associated with the tooth movement, one or more attachments/attachment profiles associated with the movement vector is determined (step 2240). Attachment parameters such as the position of the dental attachment, the angulation of the dental attachment, the surface area perpendicular to the direction of the force from the dental appliance, for example, are determined. Thereafter, the one or more attachments are positioned on the tooth for contact with the corresponding appliance during the treatment stage (step 2250). The attachment parameter profile and positioning can be customized and selected as described further herein to achieve the desired tooth movement (see, e.g., FIG. 3). In this manner, in one embodiment, the force/torque from the dental appliance is accurately applied to the tooth to reposition the tooth from the initial position to the target or second treatment stage position.

As described above, embodiments of the invention provide an attachment controlled by several parameters so that the shape of the attachment and the position of the attachment on a tooth are patient specific and provide optimal force and torque. In particular, the shape and location of the parametric patient specific attachment are determined such the following conditions are satisfied: 1) torque is provided around a long axis of the tooth with a clinically admissible magnitude; 2) a clinically reasonable extrusive force is provided; and 3) collisions of the attachment with other teeth (both of the same and opposite jaws) in intermediate stages of teeth movement are excluded. Admissible magnitudes of torque and force may be determined from orthodontic literature, expert opinions, clinical experience and results of computer simulation of tissue resistance.

Figure 19:
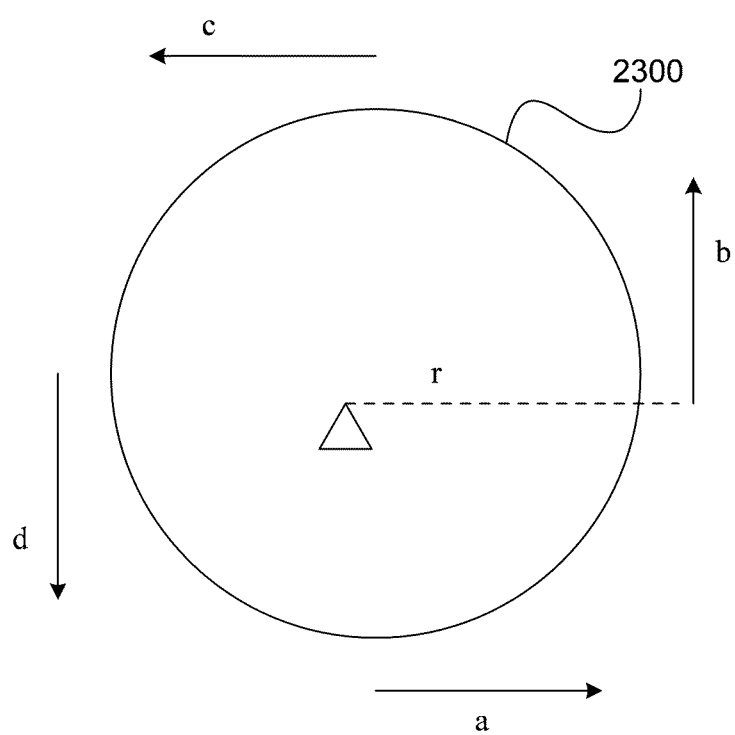
FIG. 19 illustrates object rotation by applying a force at a direction tangential to the object's rotational trajectory.

FIG. 19 illustrates that an object may be moved by applying a force along any direction tangential to the object's rotational trajectory. Specifically, a force (a, b, c or d) applied to an object 2300 can rotate the object in a circle by a torque of the cross product of an arm (r) and the amount of force (F) applied to the object, r×F. A pair of equal and opposite forces may create a torque that has a zero resultant force (e.g., forces a and c, or forces b and d). Three parameters together generate a torque: 1) a force vector, 2) a point where the force is applied, and 3) a point at which the torque is measured. The point where the force is applied and the point at which the torque is measured determine the arm vector. When rotating a tooth, the torque is calculated with respect to a center of resistance of the tooth.

Previous practice of tooth rotation was to add a standard attachment to the center of the crown, or facial axis point of the buccal surface of the tooth, and program rotation of the tooth. An attachment receiving well in an aligner is formed on the shape of the standard attachment in a thermoplastic sheet using a thermoforming process. The resulting attachment receiving well contacts the bonded attachment in certain areas resulting in a force profile that rotates the tooth while the patient wears the aligner. This conventional rotation method, however, cannot control the contact and resultant force profile consistently.

In one aspect, to address the drawbacks of the conventional standard attachment, the present invention provides an aligner activator. A major difference between the standard attachment approach and the aligner activator of the present invention lies in the creation of a contact point between the attachment body and the attachment receiving well. An activator, as used herein, can include any feature of the aligner or orthodontic system that engages an active surface of an attachment so as to apply a load to the tooth. A variety of activator structures may be utilized, with non-limiting examples including an attachment receiving well or surface thereof, dimple, ridge, body (e.g., composite) placed between an aligner and an attachment, and the like. In the standard attachment, the contact point is defined by the discrepancy of the position of the attachment body and the attachment receiving well due to the rotation of the tooth crown from an initial stage to a subsequent stage. In this case, the shape of the attachment body and the inner surface of the attachment receiving well are conformed by the thermoforming process. In accordance with embodiments of the present invention, the discrepancy of the position of the attachment body and the attachment receiving well still exists. In addition, the shape of the attachment body and the attachment receiving well are designed differently such that the attachment receiving well contacts and applies the force and torque desired clinically without the discrepancy mentioned above. In this case, the attachment/activator pair generates the desired force profile for tooth movement without any crown movement. In accordance with embodiments of the invention, the attachment/activator pair is used for upper and lower tooth rotation along a long axis of the tooth. As one having ordinary skill in the art would appreciate, however, the attachment/activator pair may be used to facilitate other orthodontic movements.

The attachment/activator pair is designed using parametric design tools corresponding to different parameters. The parameters are listed in the following Table 1 along with the corresponding function and identifying symbols of the parameters. A parametric rotation attachment with an activator configured in the aligner is abbreviated PRAA. In accordance with embodiments of the invention, the parameters may be prioritized or assigned a priority. For example, collisions may be assigned or weighted with high priority such that identification of an attachment providing good force application may be rejected where design and/or positioning would result in a collision event.

TABLE 1

| Symbol | Function | Parameters |
|---|---|---|
| Oz | Control force magnitude | origin z of PRAA |
| Oy | Control arm length | origin y of PRAA |
| P3 | Control force direction | angle between PRAA clip plane and x-y plane of tooth |
| P4 | Control force magnitude | prominence |
| P5 | Control force magnitude | angle along x-axis of PRAA |
| P6 | Control force magnitude | activation angle along y-axis of PRAA |
| P7 | Control force direction | angle between PRAA slope and x-z plane of tooth, or angle along z-axis of PRAA |
| R | Passive, and formability | radius of sphere |
| L1 | Passive, and formability | height of clip plane |

Figure 20:
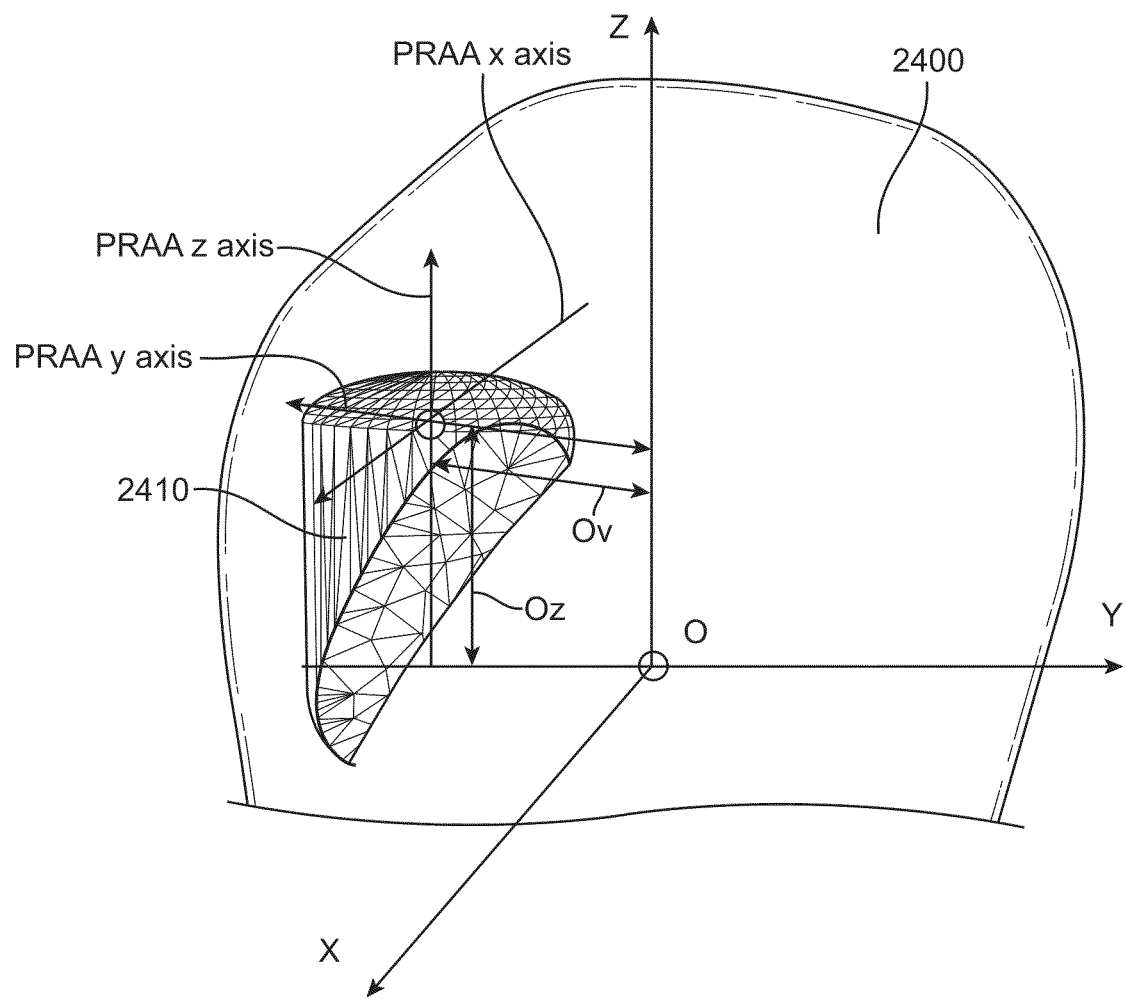
FIG. 20 illustrates a tooth with a tooth attachment formed thereon.

FIG. 20 illustrates a tooth 2400 with a tooth attachment 2410 formed thereon. The figure shows the x-axis, the y-axis, and the z-axis relative to the tooth 2400, and the PRAA x-axis, the PRAA y-axis, and the PRAA z-axis relative to the tooth attachment 2410. The figure additionally shows the origins of the y-axis (Oy) and the z-axis (Oz) for the tooth attachment 2410.

The origin of the y-axis of the PRAA (Oy) is the position of the PRAA origin along the height of the tooth crown that may affect the force output. The force may be affected because the aligner thickness, and thus strength, changes along the height of the tooth crown. By reducing the origin of the y-axis of the PRAA, the tooth attachment 2410 is closer to the gingival line where the aligner material is thinner and more flexible.

The origin of the z-axis of the PRAA (Oz) is the arm length defined as the distance between a force application point to the longitudinal axis of the tooth 2400. The origin of the z-axis of the PRAA determines how far away the ramp is from the z-axis of the tooth 2400. Therefore, this parameter controls the arm length of the torque.

The angle between the PRAA slope and the x-y plane of the tooth defines the normal of the clip plane with respect to x-y plane of the tooth with respect to the longitudinal axis of the tooth. For example, the angle between the normal of the clip plane surface and the longitudinal axis of the tooth 2400 may be 77 degrees. If a force vector (F) acts on the tooth 2400 at a 77 degree angle, the force vector may be modeled as an extrusive force of F*cos(77) and a lingual force of F*sin(77). The lingual force generates the torque around the longitudinal axis of the tooth basis, and the extrusive force prevents any intrusive tendency caused by undesired contact.

The angle between the PRAA clip plane and x-z plane of the tooth 2400 controls the orientation of the normal of the clip plane to the x-z plane of the tooth 2400. In one embodiment, this angle may be 180° at which the clip plane normal is parallel to the x-z plane. In another embodiment, this angle may be 60°. By controlling the value of this angle, the arm length may be maximized based on the location of the attachment 2410 on the tooth surface.

The prominence parameter should have a value that is sufficient to expose the designed clip plane over the crown surface while still fitting the tooth without any snapping difficulty. If the prominence value is too low, the force may be compromised because contact may be inaccurate due to the loss of area and definition on the clip plane surface in both the attachment body and the attachment receiving well. This loss of area and definition on the clip plane surface may be caused by the formability of material and manufacturing tolerance.

The activator may have a change of angle into the clip plane surface with respect to the attachment's y-axis. This angle change, referred to as the activation angle, causes contact between the activator and the clip plane surface of the attachment. The activation angle can control the force magnitude through the resultant interference between the activator and the clip plane surface of the attachment. As mentioned above, the activator results in a lingual force and an extrusive force that tend to change in a positive relationship relative to the activation angle.

A hinge in the form of a curved body allows activation on the clip plane surface without introducing undesired contact with other parts of the attachment. In one embodiment, the hinge is a spheroid defined by its origin and radius in both the attachment and the attachment receiving well. In another embodiment, the hinge is an ellipsoid defined by its origin and two axes in the attachment and a spheroid in the attachment receiving well. In the case where the hinge is a spheroid, the origin of the attachment is also the origin of the spheroid and the y-axis of the attachment extends through the sphere diameter. Thus, the activation angle along the y-axis of the attachment introduces no change on the spheroid and thus no unwanted contact. In the case where the hinge is an ellipsoid, the origin of the attachment is also the origin of the ellipsoid, the y-axis of the attachment extends through one axis of the ellipsoid, and the other axis of the ellipsoid is shorter than the spheroid diameter in the attachment receiving well. Thus, the activation angle along the y-axis of the attachment introduces no contact on the ellipsoid.

Given the hinge radius, the height of the clip plane defines the clip plane of the PRAA with respect to its own coordinate system and origin. Regardless of the angle of the clip plane, the angle between the clip plane surface and x-y plane of the tooth may be adapted to create an extrusive component. However, if the height of the clip plane is too small and the angle of the clip plane is too large, the clip plane of the PRAA will be poorly formed. In accordance with embodiments of the invention, the height of the clip plane should not be less than 3 mm.

Figure 21:
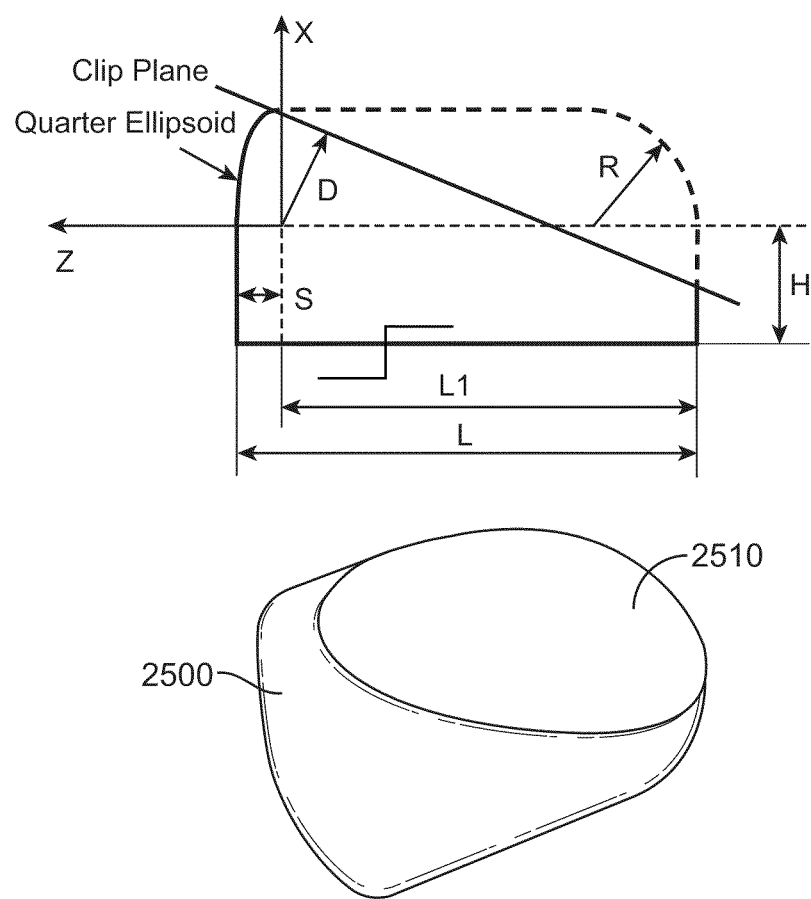
FIG. 21 illustrates a parametric activation attachment for moving a tooth.

FIG. 21 illustrates a parametric activation attachment 2500 for moving a tooth. The attachment 2500 is shaped as a quarter ellipsoid at one end with a clip plane 2510 formed on one surface thereof. Referring to the graph, the attachment 2500 is provided with different dimensions which are identified as follows: L is the attachment length, R is the radius of the sphere, S is a semi-axis of the ellipsoid, D is a vector that denotes a distance from an origin to the clip plane and to the clip plane's normal, and H is the base height.

Figure 22:
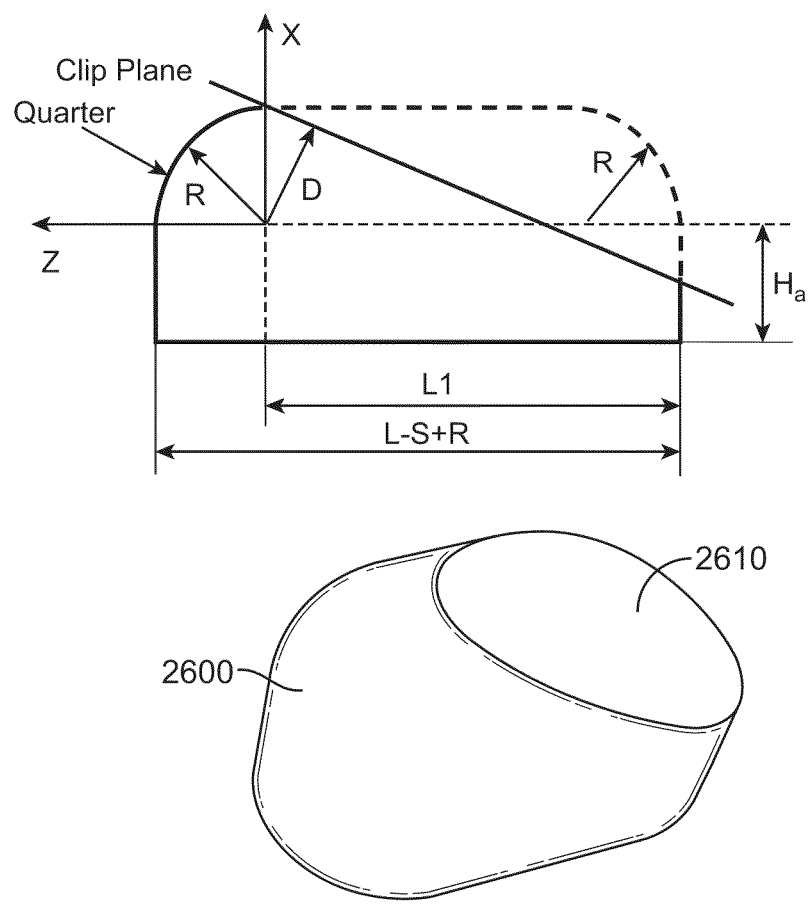
FIG. 22 illustrates an activator of an attachment for moving a tooth.
Figure 23:
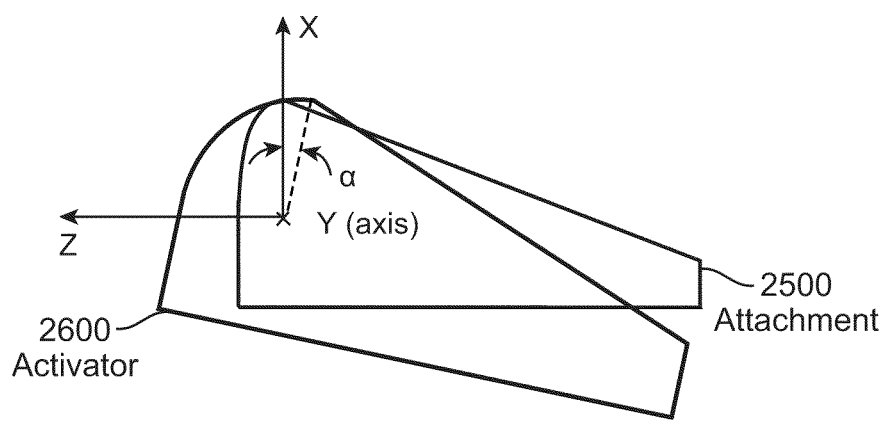
FIG. 23 illustrates the interaction between the activator and the attachment which causes a clip plane of the activator to be rotated.

FIG. 22 illustrates an activator 2600 of an attachment for moving a tooth. Specifically, the activator 2600 is provided in the aligner and is used in conjunction with the attachment 2500 formed on a tooth to rotate the tooth. The activator 2600 is shaped as a quarter sphere at one end of a top surface with a clip plane 2610 formed on an opposite end of the top surface. The activator 2600 and the attachment 2500 may each have different base heights (H, $H_a$). The orientation of the clip plane 2610 of the activator 2600 is different than the orientation of the clip plane 2510 of the attachment 2500. Referring to FIG. 23, which shows the interaction between the activator 2600 and the attachment 2500, the clip plane 2610 of the activator 2600 is rotated an angle α around a y-axis.

The following parameters are used to control the positioning of the attachment on a tooth and the activator on the aligner: 1) the origin z of PRAA (Oz) which is the distance from the attachment's origin to the facial axis of a clinical crown (FACC) point occlusally; 2) the origin of the y-axis of the PRAA (Oy) which corresponds to the arm length; 3) the angle between the attachment's clipping plane and the x-y plane of the tooth (see parameter P3 in Table 1); 4) the attachment's prominence (see parameter P4 in Table 1); 5) the activation angle (see parameter P6 in Table 1), which is the angle between the activator's clipping plane and the attachment's clipping plane; 6) the minimum distance from the attachment to the gingival curve; and 7) the tooth's interproximal margin.

Figure 24:
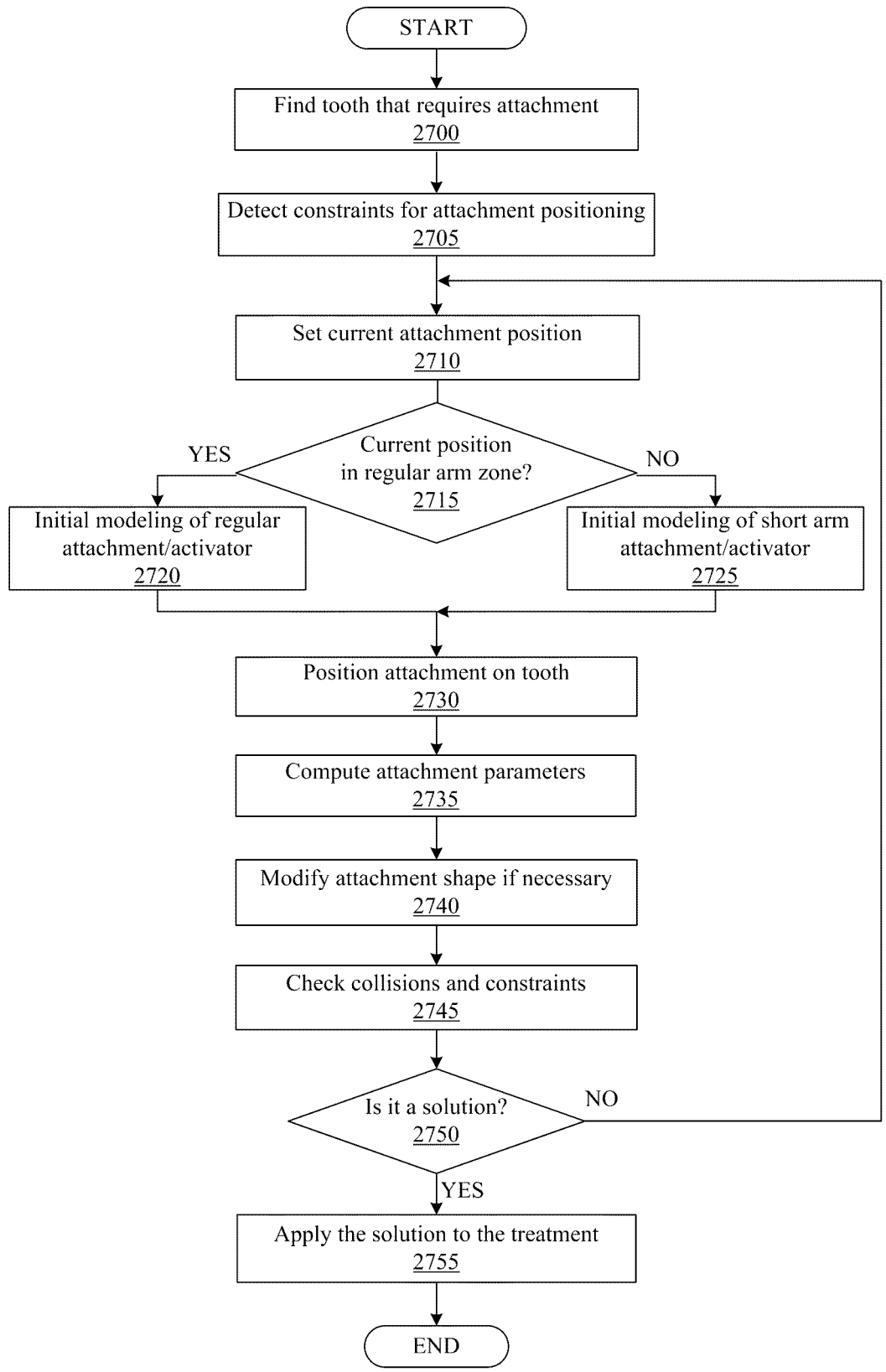
FIG. 24 is a flow diagram illustrating a method for providing a patient specific attachment and for positioning the attachment on the patient's tooth.

FIG. 24 is a flow diagram illustrating a method for providing a patient specific attachment and for positioning the attachment on the patient's tooth. The method begins by identifying a tooth that requires an attachment (step 2700). To determine whether a tooth needs an attachment, or in which stage interval a tooth requires an attachment, an algorithm is performed to compute total rotational movement. If the movement is more than a specified threshold, the tooth is identified as requiring an attachment.

Any constraints for positioning the attachment are detected (step 2705). The positioning constraints are described below with reference to FIG. 25. A current position for the attachment is then set such that the attachment is positioned inside a constrained boundary. (step 2710).

A determination is then made whether the current position of the attachment is in a regular arm zone (step 2715). If the current position of the attachment is in the regular arm zone, processing proceeds to step 2720 where the initial modeling of a regular attachment/activator pair occurs. If the current position of the attachment is not in the regular arm zone, processing proceeds to step 2725 where the initial modeling of a short arm attachment/activator pair occurs. The attachment/activator pair is patient specific and tooth specific. The shape and position of the attachment/activator pair are determined by the tooth's geometry. For example, when a tooth is large, a larger attachment may be needed. The shape parameters are used to model the initial shape of the attachment/activator pair, which may be modified if necessary. The attachment is then positioned on the tooth (step 2730).

The attachment parameters are computed based on the initial shape and position of the attachment (step 2735). Example attachment parameters include arm vector, arm length, clipping plane area, clipping plane width, and clipping plane length. The shape of the attachment is modified if any of the parameter values do not fall within a predetermined range of values (step 2740). If all of the parameter values are within the acceptable range, the shape and position of the attachment does not require modification.

Collisions and constraints are checked (step 2745). The attachment should not collide with other objects, such as other teeth or attachments, a ridge, a virtual filler, etc. In addition, the constraint thresholds should be satisfied, such as the distance to the gingival curve, the distance to the interproximial zone or region (IP zone or IPR), the distance to the incisal edge, etc.

A determination is then made if the attachment provides a solution that will result in the desired movement of the tooth. If the attachment does not provide the desired solution, processing returns to step 2710 where the position of the attachment is modified. If the attachment provides a solution that will result in the desired movement of the tooth, processing moves to step 2755 where the solution is applied to the treatment of the patient. Processing then terminates.

Figure 25:
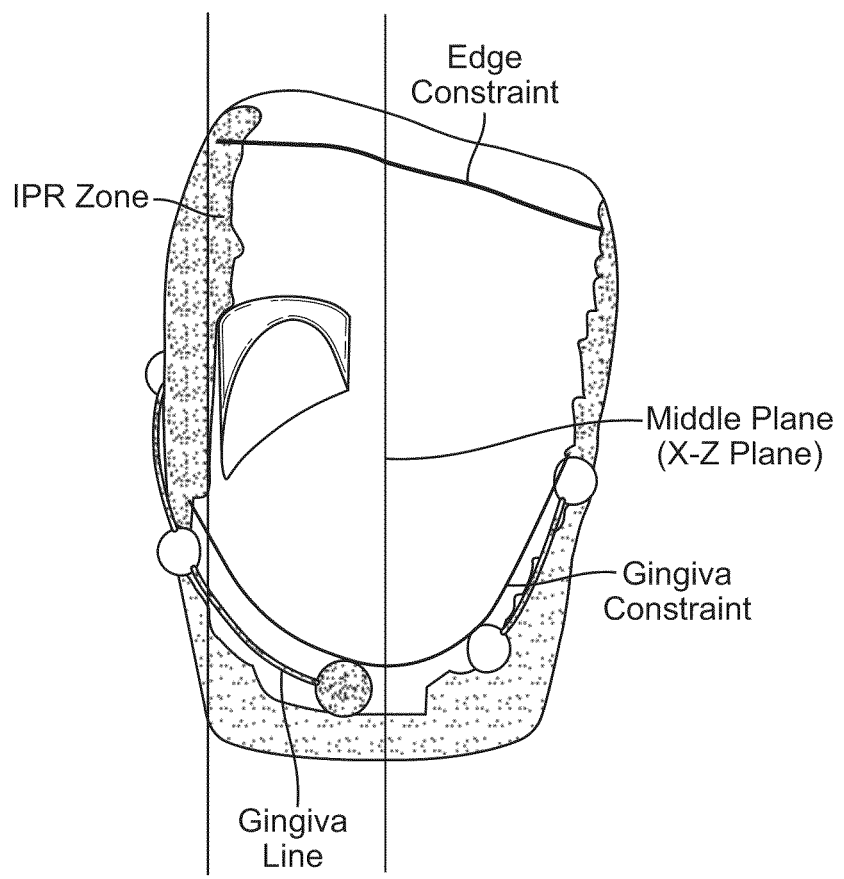
FIG. 25 illustrates positioning constraints that should be satisfied when determining a position of an attachment on a tooth.

FIG. 25 illustrates positioning constraints that should be satisfied when determining a position of the attachment on a tooth. When determining the attachment's position, the following parameters are considered: 1) gingiva line; 2) IP zone (on tooth's facial side); 3) interproximal boundary from distal/mesial extreme point; 4) middle plane (x-z plane); and 5) tooth incisal edge constraint.

Figure 26:
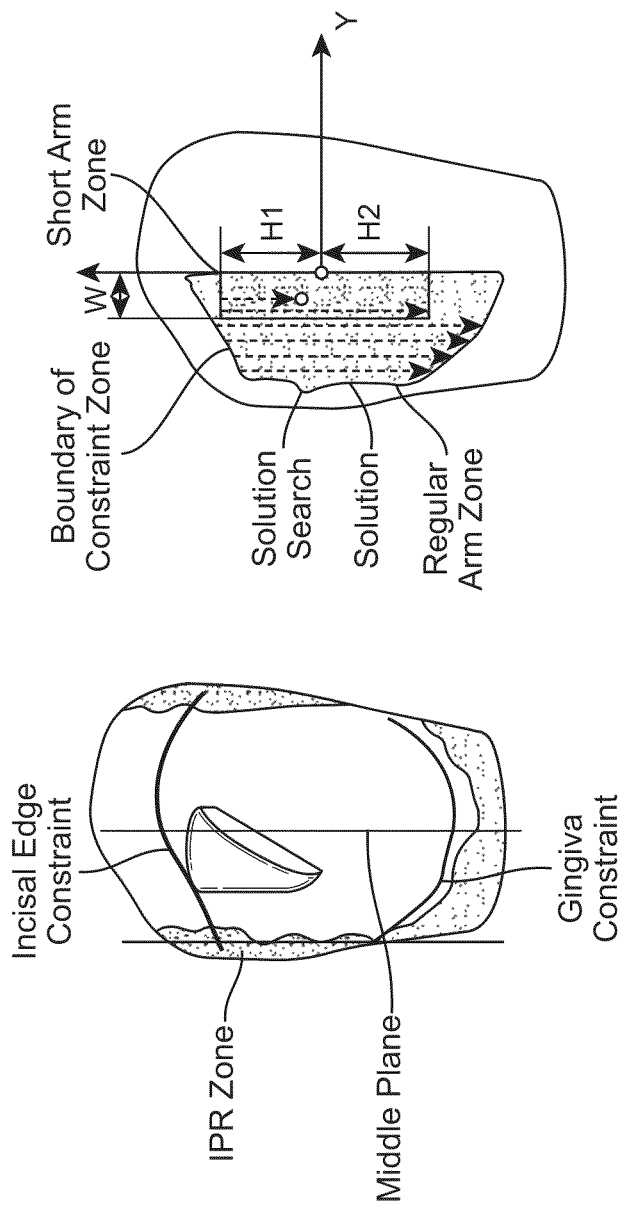
FIG. 26 illustrates different parameters on a tooth that are used in an algorithm for designing an attachment that produces adequate torque when the attachment is placed near a facial axis of a clinical crown (FACC).

To avoid collision with adjacent teeth and teeth on the opposite jaw, the attachment may need to be placed near the facial axis of a clinical crown (FACC). For both upper teeth and lower teeth, when the tooth is small, a short arm attachment is needed. When the attachment is close to the FACC, the torque may be insufficient for rotation due to the short arm. This problem is most relevant in the lower jaw. FIG. 26 illustrates different parameters on a tooth that are used in an algorithm for designing an attachment that produces adequate torque when the attachment is placed near the FACC. An algorithm for short arm attachment positioning is described below.

Step 1: The most interproximal searching line is identified. If the searching line is inside the regular arm zone, the position with a regular attachment solution is located. The searching is performed directionally from the interproximal boundary to FACC, and from the incisal edge constraint to the gingival line. The regular arm solution should meet all constraints. If the solution is found, then the solution is identified and implemented. If the solution cannot be found in the regular arm zone, Step 2 is performed to find a solution in the short arm zone.

Step 2: For each position point on the searching line, a potential solution is computed. The attachment's rotation angle is computed by a rotation angle function. The activation axis is also computed, then Step 3 is performed.

Step 3: If none of the potential solutions meet the constraints, Step 4 is performed. Otherwise, each potential solution is checked to determine that all constraints are met. The solutions that meet the constraints are compared and an optimal solution is selected. For example, the maximum value for the arm is selected as the optimal solution.

Step 4: The scan line is moved toward the FACC in increments. If the searching line is on the FACC or beyond the FACC, then a solution cannot be found and the search is terminated. If the searching line is found before the FACC is reached, Step 2 is performed to find a solution in the short arm zone.

Figure 27:
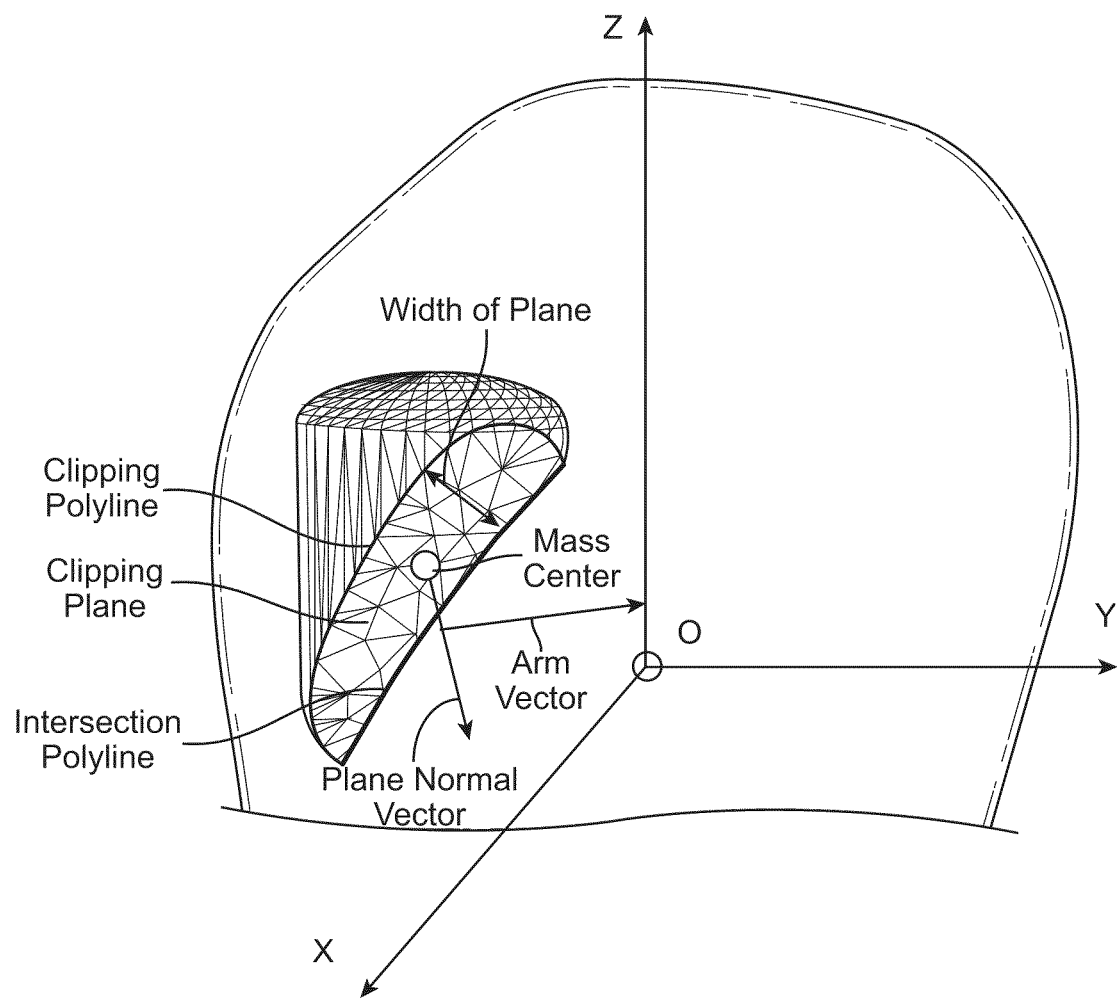
FIG. 27 illustrates different parameters of an active attachment surface.

FIG. 27 illustrates different parameters of an active attachment surface. Example parameters include: 1) an area of the clipping plane, which is bounded by a clipping polyline and intersection polyline between the clipping plane and the tooth surface; 2) a length of the intersection polyline between the clipping plane and the tooth surface; 3) a width (i.e., maximum-minimum distance) between the clipping polyline and the intersection polyline; 4) a mass center of the clipping plane; 5) an arm vector, which is perpendicular to both Oz and the clipping plane normal; 6) an arm length, which is a signed length of the arm vector depending on the rotation about Oz based on the right-hand rule; and 7) the T-value, which is computed as follows: ((−PLANE NORMAL VECTOR)*ARM VECTOR)*Z AXIS)*AREA.

Figure 28:
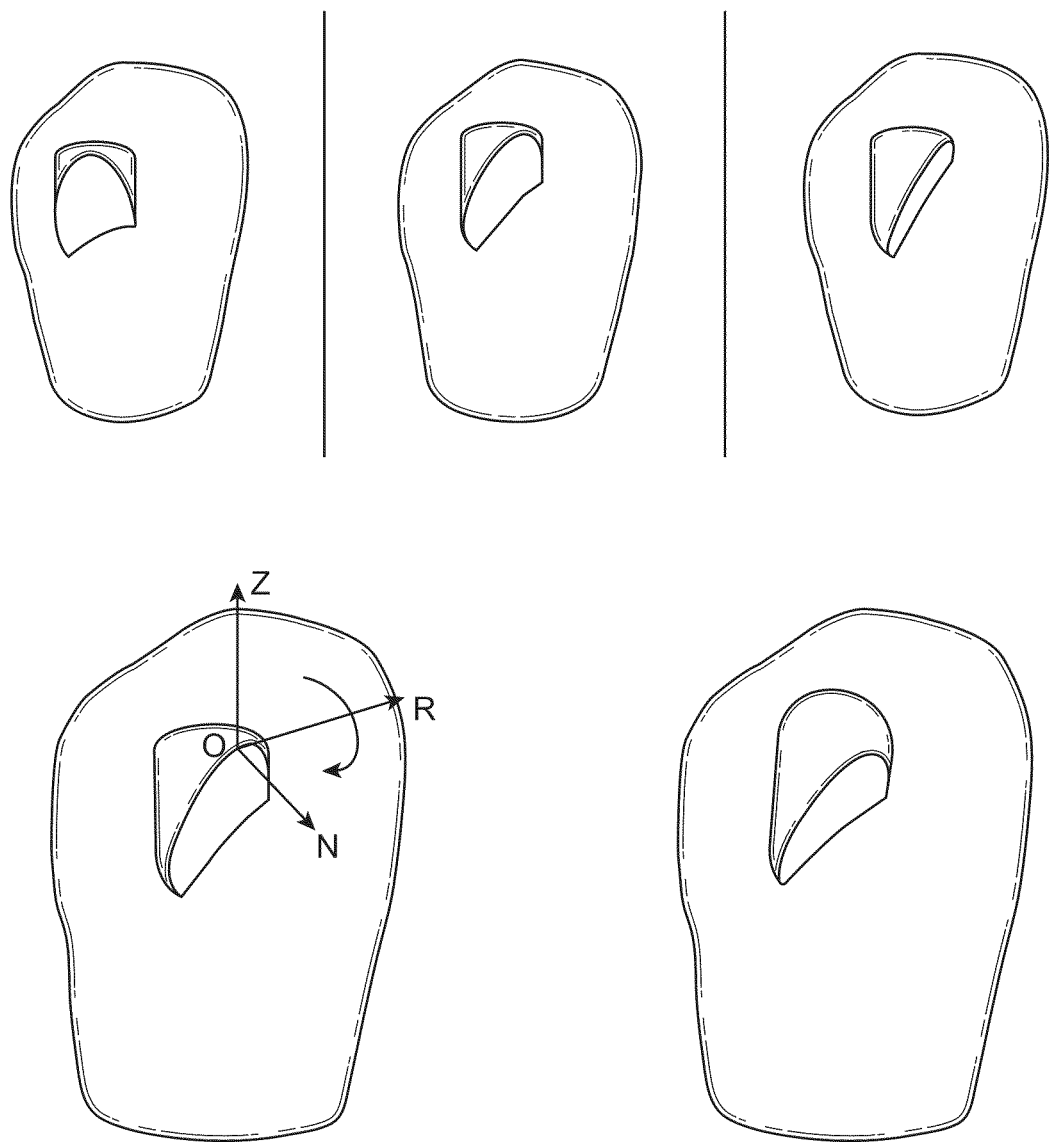
FIG. 28 illustrates a comparison of clipping plane rotation of an attachment on a tooth.

The parameters may be adjusted to compensate for the short arm. For example, rotation may occur around the z-axis of the attachment to maximize the z-component of the torque. FIG. 28 illustrates a comparison of clipping plane rotation. As shown in the upper portion of the Figure, the attachment is provided on a surface of a tooth without rotation, with a 30 degree rotation, and with a 60 degree rotation.

The activator is rotated around the activation axis. With reference to the lower portion of the Figure, the activation axis passes through the origin (O) of the attachment and is directed along the cross product (OR) between the attachment's Oz axis and a normal of the attachment's clipping plane. The lower left portion of FIG. 28 shows the attachment, and the lower right portion of FIG. 28 shows the activator with a 12 degree rotation around the activation axis (OR).

Figure 29:
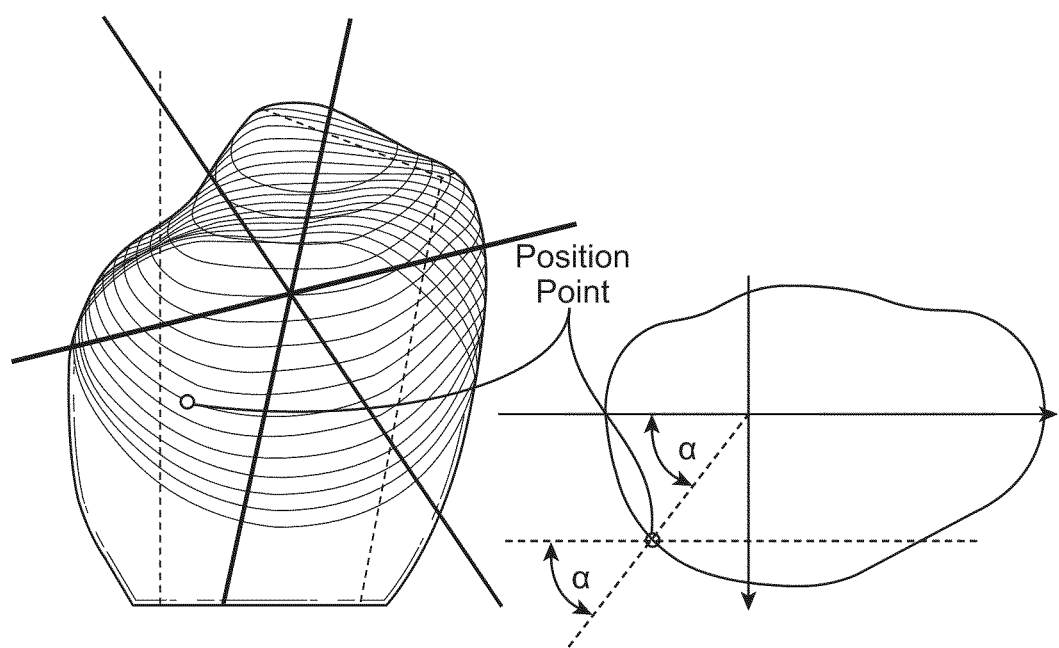
FIG. 29 illustrates an optimized rotation angle of a clipping plane of an attachment.

FIG. 29 illustrates an optimized rotation angle of the clipping plane. The corrected tooth's z-axis is utilized (internally) to measure the rotation angle of the clipping plane. The clipping plane's rotation angle may be between 0° and 60°. The optimized rotation angle is determined as follows:

$$\text{Rotation Angle} = \begin{cases} \alpha, & \alpha \leq 60° \\ 60°, & \alpha > 60° \end{cases}$$

Other parameters that may be adjusted to compensate for the short arm include: 1) parallel translation of the clipping plane to adjust the width and length of the active surface; and 2) rotation around the x-axis of the attachment to adjust the attachment width (see parameter P5 in Table 1).

During manufacture of the attachment/activator pair the following limitations should be observed: 1) The size of the spherical portion cannot be smaller than a 2 mm in diameter due to formability limitations. 2) The attachment should not create such a large overhang on the tooth surface that the material cannot conform well to the geometry. For example, if the height of the clip plane (see parameter L1 in Table 1) is too short, the angle of the clipping plane will be too large, resulting in a poorly formed clipping plane of the PRAA. Thus, the height of the clipping plane should not be less than 3 mm. 3) If the prominence is too low, the force may be compromised because the contact is not correct due to the loss of area and definition on the clipping plane surface in both the attachment body and the activator. This is caused by the formability of material and manufacturing tolerance. 4) In one embodiment, the side of the attachment is curved to provide a smooth transition to the tooth surface. This may ease material conformity while thermoforming. 5) The angle along the z-axis of the attachment (see parameter P7 in Table 1) should be within a range that avoids cracking of the material at an end opposite the hinge.

The present invention can make use of various computer implemented embodiments of the methods described herein. For example, a computer implemented method in one embodiment includes establishing an initial position of a tooth, determining a target position of the tooth in a treatment plan, calculating a movement vector associated with the tooth movement from the initial position to the target position, determining a plurality of components corresponding to the movement vector, and determining a corresponding one or more positions/profiles of a respective one or more shaped features. The shaped features may be configured to apply a predetermined force on the dental appliance substantially at the surface plane of the tooth.

An apparatus for modeling a dental appliance in another embodiment includes a data storage unit, and a processing unit coupled to the data storage unit and configured to determine an initial position of a tooth, determine a target position of the tooth in a treatment plan, calculate a movement vector associated with the tooth movement from the initial position to the target position, determine a plurality of components corresponding to the movement vector, and determine a profile and/or positioning of corresponding one or more shaped features.

The data processing aspects of the invention can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method for designing a customized tooth movement system for eliciting a selected movement of a patient's tooth, the method comprising:
    receiving, on a computer, a digital model of the patient's tooth;
    quantifying, using the computer, a desired force system for eliciting the selected tooth movement when applied to the patient's tooth;
    selecting, using the computer, a first non-custom attachment configured to engage an orthodontic appliance when worn by a patient, wherein the orthodontic appliance comprises a shell aligner;
    determining, using the computer, a first force system for application to a tooth having the first non-custom attachment and engaged with an orthodontic appliance; and
    designing, using the computer, a second custom attachment by modifying a configuration of the first non-custom attachment based on one or more patient-specific characteristics comprising tooth morphology, tooth or tooth surface orientation, or a prescribed tooth movement path, such that a second force system would be applied to a tooth having the second custom attachment and engaged with an orthodontic appliance, the second force system more closely corresponding to the desired force system than the first force system.

2. The method of claim 1, wherein the selected tooth movement comprises extrusion, intrusion, rotation, translation, or tipping.

3. The method of claim 1, wherein the selected tooth movement comprises one or more first, second or third order movements.

4. The method of claim 1, wherein the desired force system for eliciting the selected tooth movement is calculated at least partially based on data from orthodontic literature, experimental modeling, virtual modeling, clinical information, biomechanical principles, or forces on the tooth that are contrary to moving the tooth in the selected movement.

5. The method of claim 1, wherein the configuration of the first non-custom attachment is modified at least partially based on tooth morphology.

6. The method of claim 1, wherein the designing of the second custom attachment comprises determining one or more of geometry of the second custom attachment, location of the second custom attachment on the tooth, orientation of the second custom attachment on the tooth, or probability of engagement between the second custom attachment and the orthodontic appliance.

7. The method of claim 1, wherein the configuration of the first non-custom attachment is at least partially described by a parameter value selected from an identified range of values.

8. The method of claim 1, wherein the configuration of the first non-custom attachment is at least partially described by a parameter value that is modified based on a morphological feature of the patient's tooth.

9. The method of claim 1, wherein one or more of a movement of the tooth, the desired force system for eliciting the selected tooth movement, or a parameter at least partially describing the configuration of the first non-custom attachment is defined with respect to an anatomical feature reference.

10. The method of claim 9, wherein the reference comprises a long axis, an orthodontic reference point, plane or occlusal plane of the patient's dentition, one or more skeletal points or planes, or a soft tissue of the patient.

11. A method for generating a customized tooth movement system comprising a tooth attachment configured to engage an orthodontic appliance worn by a patient and apply a repositioning force system to a tooth of the patient corresponding to a selected movement of the patient's tooth, the method comprising:
    quantifying, using a computer, a desired force system to be applied to the patient's tooth so as to elicit the selected tooth movement;
    selecting, using the computer, a first non-custom attachment from a group of non-custom attachments;
    determining, using the computer, a first force system for application to a tooth having the first non-custom attachment and engaged with an orthodontic appliance; and
    designing, using the computer, a second custom attachment by modifying one or more attributes of the first non-custom attachment such that a second force system would be applied to the tooth having the second custom attachment and engaged with an orthodontic appliance worn by the patient, wherein the second force system more closely corresponds to the desired force system to be applied to the patient's tooth so as to elicit the selected tooth movement than the first force system, wherein the orthodontic appliance comprises a shell aligner.

12. A method for designing a customized tooth movement system comprising one or more tooth attachments for eliciting a selected movement of a patient's tooth, the method comprising:
    quantifying, using a computer, one or more forces or torques for eliciting the selected tooth movement when applied to the patient's tooth;
    selecting, using the computer, a first non-custom attachment configured to engage an orthodontic appliance when worn by a patient; and
    designing, using the computer, a second movement specific or patient-customized attachment configured to engage an orthodontic appliance when worn by a patient and apply, in conjunction with the orthodontic appliance, a repositioning force to the tooth, the second movement specific or patient-customized attachment having a configuration that has been modified from the first non-custom attachment based on the one or more forces and/or torques for eliciting the selected tooth movement to the patient's tooth such that an applied repositioning force substantially matches the one or more forces or torques for eliciting the selected tooth movement to the patient's tooth, wherein the orthodontic appliance comprises a shell aligner.

13. A method for designing a customized tooth movement system, comprising:
    identifying, using a computer, a range of force or torque values corresponding to a force system to be applied to a tooth so as to elicit a selected tooth movement;

modeling, using the computer, a first force or torque value applied to a tooth when a first non-custom attachment disposed on the tooth is engaged with an orthodontic appliance, the first non-custom attachment having a configuration affecting a force or torque applied to the tooth during engagement, wherein the first force or torque value is identified as being within the range of values; and designing, using the computer, a second custom attachment by modifying the first non-custom attachment configuration such that a second force or torque value is applied to a tooth having the second custom attachment and engaged with an orthodontic positioning appliance, wherein the second force or torque value is higher or lower in the range of values compared to the first force or torque value and selected to produce force or torque application to a tooth during orthodontic treatment, wherein the orthodontic appliance comprises a shell aligner.

14. The method of claim 13, wherein the selected tooth movement comprises an intrusion, extrusion, rotation, translation or tipping.

15. The method of claim 13, wherein the second custom attachment is beveled incisally or gingivally and modifying the first non-custom attachment configuration comprises modifying a surface angle of a bevel on the first non-custom attachment.

16. The method of claim 13, wherein the selected tooth movement is an extrusion, the first non-custom attachment is beveled gingivally, and modifying the first non-custom attachment configuration comprises modifying a surface angle of a bevel on the first non-custom attachment.

17. An orthodontic repositioning system, comprising the second custom attachment as in claim 13, and an orthodontic appliance configured to engage the second custom attachment when the second custom attachment is disposed on the patient's tooth and the appliance is worn by the patient.

18. A method for designing a custom attachment for eliciting a selected movement of a patient's tooth, the method comprising:
    identifying, using a computer, an initial position and configuration of a non-custom attachment on a tooth at a location on a digital model of the patient's dentition;
    computing, using the computer, attachment parameters based on the initial position and configuration of the non-custom attachment and a geometry of the tooth, wherein each attachment parameter is associated with a predetermined range of values corresponding to a selected force or a selected torque for the selected movement of the tooth when engaged with a shell aligner having at least one tooth receiving cavity configured to receive and resiliently move the tooth and in the event that at least one value of the computed parameters is not within the predetermined range of values, modifying the configuration of the non-custom attachment such that all of the attachment parameters are within the predetermined range of values which elicit the selected movement of the patient's tooth.

19. The method of claim 18, wherein the non-custom attachment is modified with respect to at least one of: an arm vector, an arm length, a clipping plane area, a clipping plane width, or a clipping plane length.

20. The method of claim 18, wherein the non-custom attachment is modified such that the custom attachment does not collide with an object throughout all or a portion of treatment of the tooth.

21. The method of claim 20, wherein the object comprises one of another tooth, an orthodontic attachment on a tooth, or an appliance.

22. The method of claim 20, further comprising: prioritizing the attachment parameters comprising assigning a higher priority to attachment parameters that result in collision of the tooth with another tooth during the selected movement.

23. The method of claim 18, further comprising:
    re-modifying the configuration of the custom attachment when the custom attachment at the modified configuration does not provide a solution that results in the selected movement of the patient's tooth without collision between the custom attachment and an object throughout all of a portion of treatment of the tooth.

24. The method of claim 23, wherein the object comprises one of another tooth, an orthodontic attachment on a tooth, or an orthodontic appliance.

25. A computer program product having a computer readable medium storing a set of code modules which when executed by a processor of a computer system cause the processor to model a custom attachment for eliciting a selected movement of a patient's tooth, the computer program product comprising;
    code for identifying an initial position and configuration of a non-custom attachment on a tooth at a location on a digital model of the patient's dentition;
    code for computing attachment parameters based on the initial position and configuration of the non-custom attachment and geometry of the tooth, wherein each attachment parameter is associated with a predetermined range of values corresponding to a selected force or a selected torque for the selected movement of the tooth when engaged with a shell aligner having at least one tooth receiving cavity configured to receive and resiliently move the tooth; and
    code for modifying the configuration of the non-custom attachment such that all of the attachment parameters are within the predetermined range of values which elicit the selected movement of a patient's tooth.

* * * * *